US006942660B2

(12) United States Patent
Pantera et al.

(10) Patent No.: US 6,942,660 B2
(45) Date of Patent: Sep. 13, 2005

(54) ELECTROSURGICAL GENERATOR AND METHOD WITH MULTIPLE SEMI-AUTONOMOUSLY EXECUTABLE FUNCTIONS

(75) Inventors: Jim Pantera, Brighton, CO (US); Ronald Shores, Greenwood Village, CO (US); Richard Thompson, Centennial, CO (US); Rodney Davis, Parker, CO (US); Geoffrey W. Dolan, San Francisco, CA (US)

(73) Assignee: ConMed Corporation, Utica, NY (US)

( * ) Notice: Subject to any disclaimer, the term of this patent is extended or adjusted under 35 U.S.C. 154(b) by 138 days.

(21) Appl. No.: 10/299,953

(22) Filed: Nov. 19, 2002

(65) Prior Publication Data

US 2004/0097914 A1 May 20, 2004

(51) Int. Cl.[7] ................................................ A61B 18/18

(52) U.S. Cl. ......................................... 606/34; 606/38

(58) Field of Search .......................... 606/32–35, 37–42

(56) References Cited

U.S. PATENT DOCUMENTS

| | | | |
|---|---|---|---|
| 3,963,030 A | 6/1976 | Newton | |
| 4,349,704 A | 9/1982 | Gills | |
| 4,416,276 A | 11/1983 | Newton et al. | |
| 4,416,277 A | 11/1983 | Newton et al. | |
| 4,429,694 A | 2/1984 | McGreevy | |
| 4,438,766 A | 3/1984 | Bowers | |
| 4,559,943 A | 12/1985 | Bowers | |
| 4,569,345 A | 2/1986 | Manes | |
| 4,573,466 A | 3/1986 | Simada et al. | |
| 4,574,311 A | 3/1986 | Resnikoff et al. | |
| 4,590,934 A | 5/1986 | Malis et al. | |
| 4,617,927 A | 10/1986 | Manes | |
| 4,658,819 A | 4/1987 | Harris et al. | |
| 4,658,820 A | 4/1987 | Klicek | |
| 4,727,874 A | 3/1988 | Bowers et al. | |
| 4,739,759 A | 4/1988 | Rexroth et al. | |
| 4,893,341 A | 1/1990 | Gehring | |
| 4,961,047 A | 10/1990 | Carder | |
| 4,961,739 A | 10/1990 | Thompson | |
| 5,167,660 A | 12/1992 | Altendorf | |
| 5,290,283 A | 3/1994 | Suda | |
| 5,300,068 A | 4/1994 | Rosar et al. | |
| 5,318,563 A | * 6/1994 | Malis et al. | ............... 606/38 |
| 5,370,645 A | * 12/1994 | Klicek et al. | ............... 606/35 |
| 5,372,596 A | 12/1994 | Klicek et al. | |
| 5,422,567 A | 6/1995 | Mastunaga | |
| 5,599,344 A | 2/1997 | Paterson | |
| 5,602,847 A | 2/1997 | Pagano et al. | |
| 5,793,801 A | 8/1998 | Fertner | |

(Continued)

OTHER PUBLICATIONS

International Search Report for the PCT application PCT/US03/33783 which corresponds to the present U.S. application.

H. Hölscher et al., *Microcomputers in Safety Technique, An Aid to Orientation for Developer and Manufacturer*, 1986, Chapter 1–1 through 8–9.

*Primary Examiner*—Michael Peffley
(74) *Attorney, Agent, or Firm*—John R. Ley

(57) ABSTRACT

Semi-autonomously executed routines accomplish the primary functions of electrosurgical energy delivery on a responsive basis for power control purposes and to adapt the delivered output waveform to perform new and better surgical procedures. The routines include and output voltage and output current sampling routine, a control routine for establishing the width of drive pulses used to create the output waveform, a pattern generation routine for establishing the pattern of drive pulses to be delivered in one mode cycle established by a selected mode of operation, a pattern delivery routine for repeatedly delivering sequences of the mode cycle pattern of drive pulses, and a power supply control routine for varying the voltage of the drive pulses in coordination with varying the width of the drive pulses.

73 Claims, 10 Drawing Sheets

U.S. PATENT DOCUMENTS

| | | |
|---|---|---|
| 6,010,499 A | 1/2000 | Cobb |
| 6,123,702 A | 9/2000 | Swanson et al. |
| 6,183,468 B1 | 2/2001 | Swanson et al. |
| 6,228,079 B1 | 5/2001 | Koenig |
| 6,245,065 B1 | 6/2001 | Panescu et al. |
| 6,322,555 B1 | 11/2001 | LaHaye |
| 6,398,779 B1 | 6/2002 | Buysse et al. |
| 6,402,742 B1 | 6/2002 | Blewett et al. |
| 6,416,509 B1 * | 7/2002 | Goble et al. .................. 606/37 |
| 2001/0056276 A1 | 12/2001 | LaHaye |
| 2002/0016691 A1 | 2/2002 | Kameda et al. |
| 2002/0022836 A1 | 2/2002 | Goble et al. |

* cited by examiner

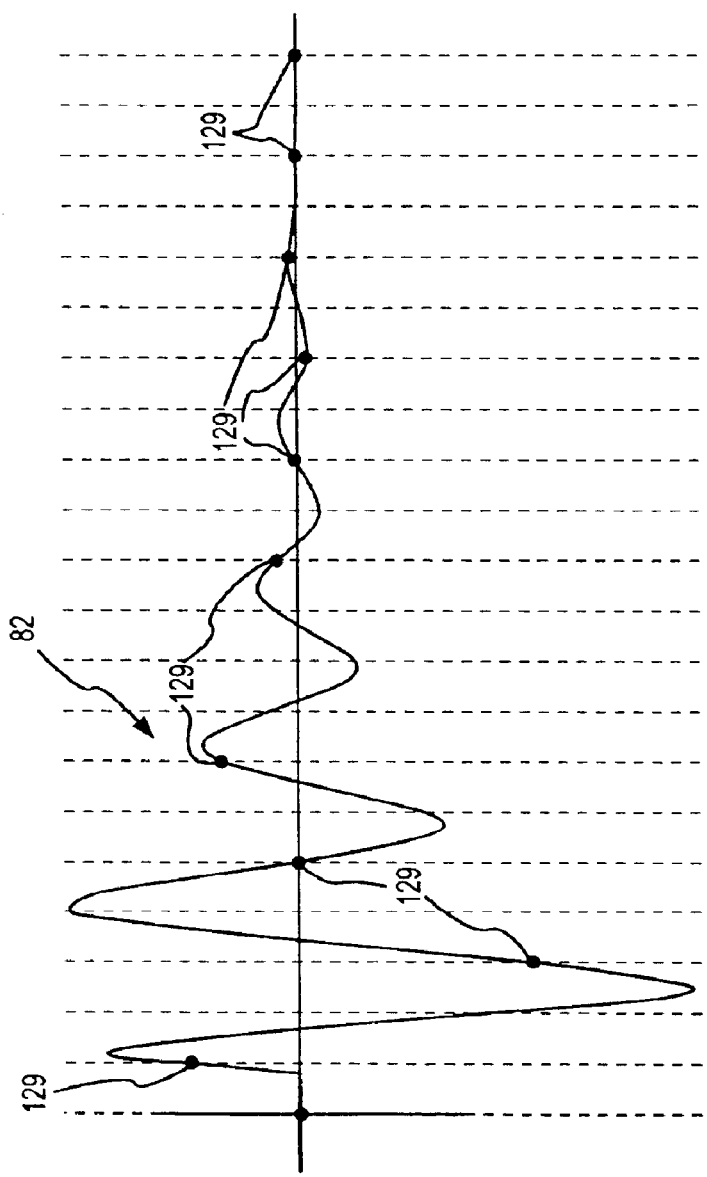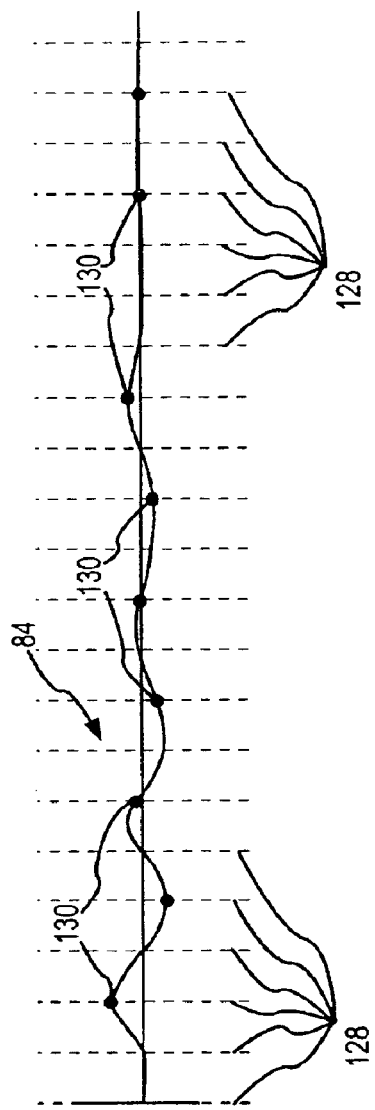

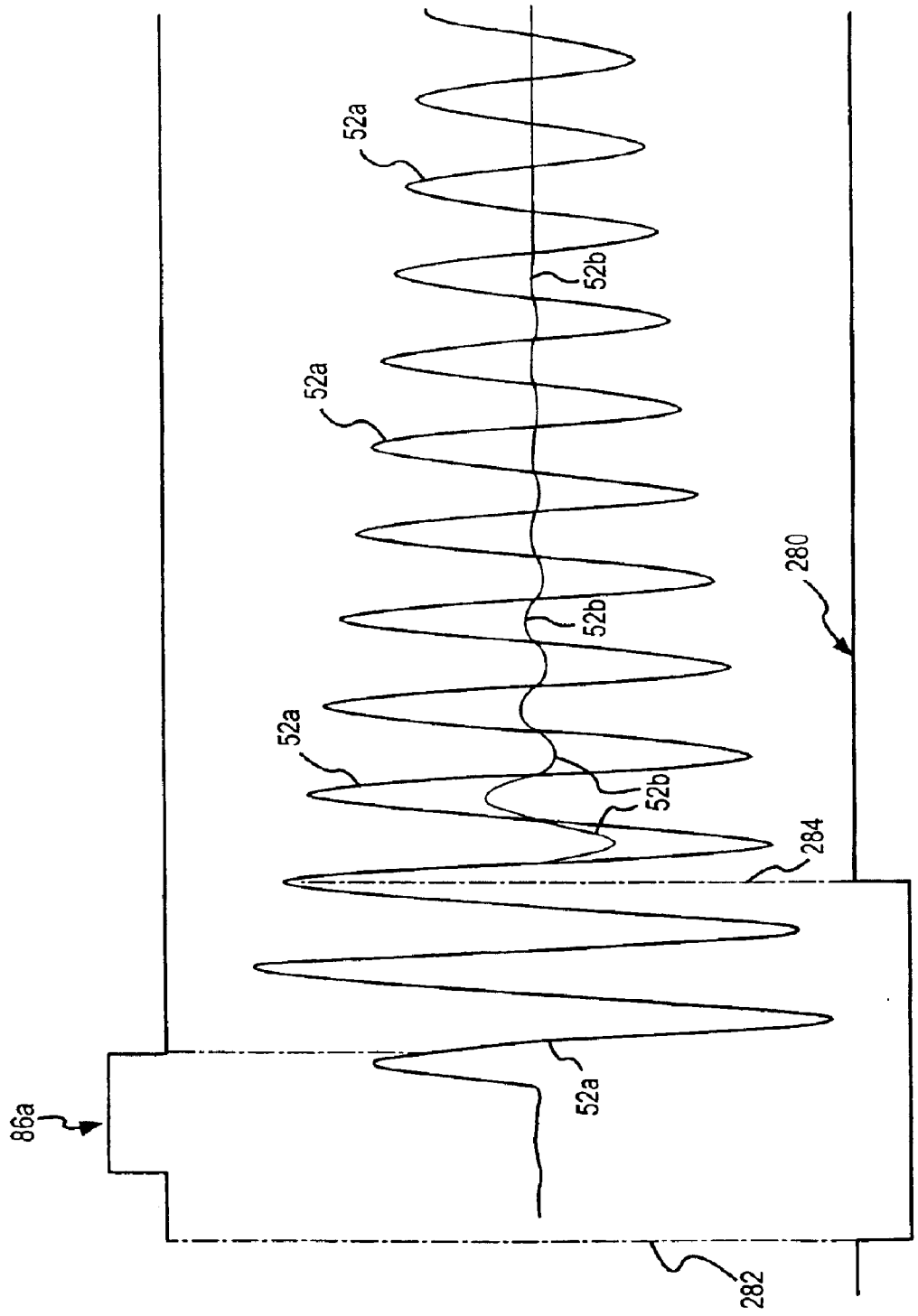

ELECTROSURGICAL GENERATOR AND METHOD WITH MULTIPLE SEMI-AUTONOMOUSLY EXECUTABLE FUNCTIONS

CROSS-REFERENCE TO RELATED APPLICATIONS

This invention and application is related to inventions for an Electrosurgical Generator and Method with Voltage and Frequency Regulated High Voltage Current Mode Power Supply, Ser. No. 10/299,951 and an Electrosurgical Generator and Method for Cross-Checking Mode Functionality, Ser. No. 10/299,952, both of which were filed Nov. 19, 2002 and assigned to the assignee of the present invention. The disclosures of these U.S. patent applications are incorporated herein by this reference.

FIELD OF THE INVENTION

This invention generally relates to electrosurgery, and more specifically, to a new and improved electrosurgical generator and method of generating electrosurgical power which makes advantageous use of a number of semi-independent and semi-autonomously executed control functions or routines to create flexibility and adjustability in the performance in the electrosurgical generator and method of power delivery for the purpose of enhanced power regulation, more precise control over functionality and adaptation to accommodate new and enhanced surgical procedures, among other things.

BACKGROUND OF THE INVENTION

Electrosurgery involves applying relatively high voltage, radio frequency (RF) electrical power to tissue of a patient undergoing surgery, for the purpose of cutting the tissue, coagulating or stopping blood or fluid flow from the tissue, or cutting and coagulating the tissue simultaneously. The high voltage, RF electrical power is created by an electrosurgical generator, and the electrical power from the generator is applied to the tissue from an active electrode manipulated by a surgeon during the surgical procedure.

The amount and characteristics of the electrosurgical power delivered to the patient is determined by the type of surgical procedure performed and the amount of electrosurgical output power required, as well as the tissue characteristics of the patient. Selecting the cutting mode of operation causes the electrosurgical generator to continuously deliver relatively high RF power of moderate voltage. Selecting the coagulation mode of operation causes the electrosurgical generator to repetitively deliver relatively short bursts of high voltage, resulting in a relatively low average output power delivery. Selecting the "blend" mode of operation causes the electrosurgical generator to deliver output power having characteristics which are related to both cutting and coagulation. The blend mode of operation involves repetitively delivering relatively longer bursts of somewhat lower voltage RF output power, resulting in a relatively moderate average output power delivery. In the cut mode, for example, the continuous power output may be as high as 300 watts with an open circuit output voltage in the neighborhood of 2,000 volts peak to peak. In the coagulation mode, the bursts may reoccur at a frequency of approximately 30 kHz, have a time duration of approximately 3 microseconds, and have a peak to peak voltage of approximately 10,000 volts. A typical blend mode will involve bursts at the same frequency of approximately 30 kHz, but with time duration of approximately 5–7 microseconds and at a peak to peak voltage of approximately 4,000 volts. The higher voltage required for coagulation and blend is necessary to cause longer arcs of electrical power to jump from the active electrode to the tissue. Lower output voltage is used for cutting because long electrical arcing is not as important or necessary for cutting.

The electrosurgical generator should also have the capability to deliver these types of RF electrosurgical power under a wide variety of different and rapidly changing output conditions. The impedance of the tissue into which the RF output power is delivered may change substantially from point-to-point as the active electrode is moved during the surgical procedure. For example, a highly fluid-perfused tissue such as the liver may exhibit a resistance or impedance in the neighborhood of 40 ohms. Other tissues, such as skin which has very little moisture content, or the marrow of bone because of its physiology, have an impedance in the neighborhood of 1000–2000 ohms. Average tissue impedances range in the neighborhood of approximately 500 ohms, although the fat or adipose content of the tissue increases its impedance.

The power transfer or delivery capabilities of an electrosurgical generator, like any other power amplifier, depends on the output load characteristics into which the power is transferred. The most efficient power transfer occurs when the internal impedance characteristic of the power amplifier is matched to the external impedance into which it delivers power. Since the internal impedance characteristic of the usual electrosurgical generator cannot be matched to the widely varying tissue impedance into which the electrosurgical power must be transferred, the electrosurgical generator should have the capability to deliver relatively higher amounts of power to compensate for the usual mismatch between the internal generator impedance and the widely varying values of the external tissue impedance, and to do so on an almost instantaneously changing basis as the surgeon moves through and works with the different types of tissues at the surgical site.

Further still, an electrosurgical generator must deliver the RF electrosurgical power under tightly regulated and precisely controlled conditions. Any attempt to meet the rapidly changing power requirements cannot be accompanied by output RF electrosurgical power which causes damage to the tissue or injury to the patient or surgical personnel. Rapid and reliable control over the delivered power is essential to safe and dependable performance of the surgical procedures. Very few, if any, electrosurgical generators have the capability to meet all of these requirements, regardless of how well these requirements are understood. Indeed, almost no other electrical amplifier or power supply is subject to such widely varying requirements.

Most electrosurgical generators have relatively fixed operational features with only traditional and somewhat limited functional capabilities available for selection and use by the surgeon. For example, almost all electrosurgical generators permit the surgeon to choose output delivery characteristics which will accomplish cutting, coagulating or blended operation, and almost all electrosurgical generators permit selection and adjustment of the amount of power to be delivered in each of the selected modes of operation. However, beyond these traditional options, most electrosurgical generators do not have the capability to perform newly-developed specialized procedures which may require delivery of an electrosurgical output waveform having somewhat different characteristics than those available from a standard electrosurgical generator. Instead, limited use electrosurgical generators having such specialized output power characteristics are usually developed specifically for such procedures. On the other hand, specialized generators are generally not capable of more generalized surgical performance required from a more conventional electrosurgical generator, so the specialized generators cannot be used as substitutes of the general purpose generators.

Because the cost of an electrosurgical generator is significant, most hospitals and surgical operating facilities have only general-purpose electrosurgical generators on hand for surgical procedures. Once acquired, an electrosurgical generator is expected to have a usable lifetime extending many years and will not usually be replaced with a newer model for many years.

SUMMARY OF THE INVENTION

The present invention relates to an electrosurgical generator and method of the delivering electrosurgical power which executes the primary functions of power delivery and power regulation in such a way that all of the primary functions receive adequate computational resources to perform in a reliable, timely and safe manner without compromising performance or safety. Each of the primary functions is defined primarily by executable code or software. Executing these primary functions with software permits those primary functions to be changed, enhanced or further developed to accommodate new surgical procedures and to better accommodate existing surgical procedures. An inherent and ongoing flexibility and adaptability is achieved which permits the ability to accomplish the new surgical techniques without the necessity of replacing the entire electrosurgical generator or without incurring substantial expense for upgrading the generator. Moreover, because of the flexibility achieved from executing the primary functions from software, one electrosurgical generator can be caused to perform specialized procedures as well as more straightforward and traditional electrosurgical procedures. The flexibility and adaptability provided by this approach to controlling an electrosurgical generator and a method of delivering electrosurgical energy avoids obsolescence and facilitates the use of the most advanced surgical procedures. All of these improvements, and others, are accomplished without compromising the responsiveness or the performance characteristics, because the primary functions are organized and executed in a way which do not negatively impact the performance of the other primary functions.

In accordance with these and other improvements, the present invention relates to an electrosurgical generator having selectable modes of operation and selectable output power levels within the selected modes. Drive pulses are used to create and deliver an electrosurgical output waveform defined by output voltage and output current. The electrosurgical generator executes a sampling routine, which obtains sample values representative of output voltage and output current; a pulse control routine, which establishes a value defining the drive pulses based on the sample values and a selected output power level; a pattern generation routine, which generates a mode cycle pattern of drive pulses having the value established by the pulse control routine and in accordance with a selected mode of operation; and a pattern delivery routine, which creates drive pulses by sequentially delivering multiple mode cycle patterns generated by the pattern generation routine.

A method aspect of the present invention involves delivering an electrosurgical output waveform defined by output voltage and output current. The method comprises selecting a modes of operation to characterize the electrosurgical output waveform, selecting an output power level within the selected mode, using drive pulses to create and deliver the output waveform, obtaining sample values of the output voltage and the output current over a sampling interval, establishing a value defining the drive pulses based on the sample values and the selected output power level, generating a mode cycle pattern of drive pulses having the value defining the drive pulses in accordance with the selected mode, and sequentially delivering multiple generated mode cycle patterns to create the drive pulse.

Additional aspects of both the electrosurgical generator and the method of delivering the electrosurgical output waveform include routines and functions which establish a voltage level and the width of the drive pulses and coordinate the voltage level with the width of the drive pulses, which dynamically adjust the width and the voltage level of the drive pulses during the delivery of the output waveform, which dynamically adjust the voltage level of the drive pulses at a slower rate than the width of the drive pulses is dynamically adjusted, which obtain the sample values while establishing the value defining the drive pulses and while generating the mode cycle pattern and while generating the mode cycle pattern, which obtain the sample values of the output voltage and output current at a sampling rate which is less than the Nyquist rate for the output waveform, which change the width of at least one of a plurality of drive pulses within the mode cycle pattern after the width of those pulses has been initially established but before delivering the mode cycle pattern to thereby adjust average power over the mode cycle pattern to a value that cannot be achieved by each of the drive pulses themselves, and which selectively dissipate energy previously used to create the output waveform after the commencement of the output waveform to thereby damped or change the characteristics of the output waveform after it has commenced.

The independent routines and method functions allow the primary functions of the electrosurgical generator to be broken down and accomplished on a semi-independent and semi-autonomously executed basis, preferably by execution of code in a processor in such a way that all of the primary functions are fully responsive to control the output power while providing flexibility to adapt the performance and output characteristics to new and improved surgical procedures.

A more complete appreciation of the scope of the present invention and the manner in which it achieves the above-noted and other improvements can be obtained by reference to the following detailed description of presently preferred embodiments taken in connection with the accompanying drawings, which are briefly summarized below, and by reference to the appended claims.

BRIEF DESCRIPTION OF THE DRAWINGS

FIGS. 9 and 10 are time-expanded illustrations of an exemplary analog voltage feedback signal and an exemplary analog current feedback signal describing the electrosurgical output waveform shown in FIG. 1, respectively, illustrating sample points and sample values obtained by execute a sampling routine shown in FIG. 6.

FIG. 16 is a waveform diagram illustrating a spray coagulation drive pulse delivered to a RF power amplifier of the electrosurgical generator shown in FIG. 1.

FIG. 17 is an illustration of two superimposed output waveforms from the electrosurgical generator shown in FIG. 1, showing the effects with and without a damping functionality achieved by present invention and coordinated in time relative to the drive pulse shown in FIG. 16.

FIG. 18 is an illustration of a damping waveform, shown in a time coordinated relationship to FIG. 16 and 17, illustrating the effects of damping in creating one of the output waveforms shown in FIG. 17.

DETAILED DESCRIPTION

Figure 1:
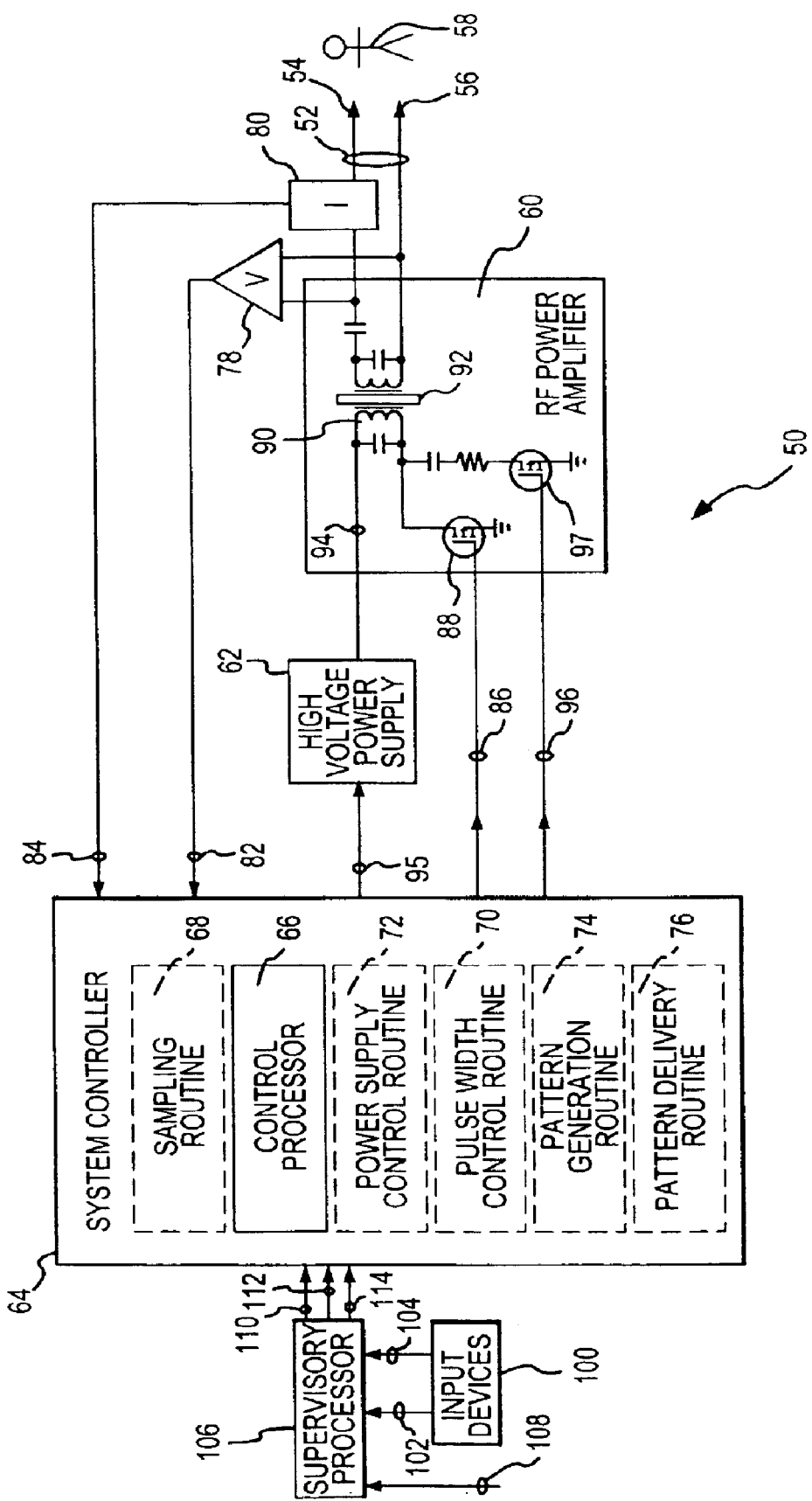
FIG. 1 is a block diagram of an electrosurgical generator incorporating the present invention.

An electrosurgical generator 50, shown in FIG. 1, creates a radio frequency (RF) electrosurgical energy output waveform 52 at output terminals 54 and 56. The RF electrosurgical output waveform from the terminals 54 and 56 is applied to the tissue of a patient 58 during an electrosurgical procedure by conventional handpieces and other instruments (not shown) connected to the terminals 54 and 56. An RF power amplifier 60 creates and supplies the RF electrosurgical power output waveform 52. Electrical energy is supplied to the RF power amplifier 60 from a high voltage power supply 62. The high voltage power supply 62 receives electrical power from commercial alternating current (AC) power distribution mains (not shown).

A system controller 64 controls the functionality of the RF power amplifier 60 and the high voltage power supply 62, to create and control the characteristics of the electrosurgical output waveform 52. The system controller 64 includes a control processor 66 which executes or controls the execution of five primary, semi-independent and semi-autonomously executing control functions or control routines: an output power sampling routine 68, a pulse width control routine 70, a power supply control routine 72, a pattern generation routine 74 and a pattern delivery routine 76. These routines permit the electrosurgical generator 50 to perform essentially all electrosurgical operations and functions. Because each of these routines is based primarily upon the execution of instructions by the control processor 66 and other digital components, the electrosurgical generator 50 can be adapted to perform a variety of electrosurgical operations and functions by writing new code defining these routines.

The sampling routine 68 develops information which describes the output power delivered from the electrosurgical generator. The output power delivery information is used primarily as feedback information for regulating and controlling the amount of electrosurgical power delivered from the output waveform 52. The sampling routine 68 develops the output power information by responding to the output voltage and output current of the output waveform 52, sensed by a voltage sensor 78 connected between the output terminals 54 and 56 and a current sensor 80 connected in series with the terminal 54, respectively. The voltage sensor 78 delivers an analog voltage feedback signal 82, and the current sensor 80 delivers an analog current feedback signal 84. The analog voltage and feedback signals 82 and 84 define and describe the output characteristics of the output waveform 52.

The pulse width control routine 70 creates a pulse width count signal which forms the primary basis for defining and establishing the width of drive pulses 86 which are applied to the RF power amplifier 60. The pulse width count signal relates to a number of quantizing intervals, each of which is a fixed amount of time in width. The value of the pulse width count signal therefore specifies the width of the drive pulse 86 which is ultimately created by the system controller 74 and supplied to the RF power amplifier 60.

The RF power amplifier includes a drive transistor 88 which conducts current through a conventional primary resonant circuit 90 of an output transformer 92. The resonant circuit 90 is formed by a capacitor connected in parallel with the primary winding of the output transformer 92, as well as other values coupled from a secondary winding of the output transformer 92 to the primary winding and other values associated with the characteristics of the output transformer 92. Current from the high voltage power supply 62 is conducted through the resonant circuit 90 when the drive transistor 88 is conductive in response to a drive pulse 86. The current conducted through the resonant circuit by the conductive drive transistor 88 stores energy in the resonant circuit 90. The amount of energy stored in the resonant circuit is determined by the time width of the drive pulse 86, and by an output voltage 94 from the high voltage power supply 62. The time width of the drive pulse 86 corresponds to the amount of time that the drive transistor 88 is conductive, and that conductivity time relates directly to the amount of energy stored in the resonant circuit 90. The output voltage 94 from the high voltage power supply 62 also directly relates to the amount of energy stored in the resonant circuit 90, because a higher voltage results in more energy transferred to the resonant circuit 90.

When the drive transistor 88 ceases conducting, the energy stored in the resonant circuit creates oscillations, and the current and voltage associated with those oscillations are inductively coupled to the secondary winding of the output transformer 92. The current and voltage at the secondary winding of the output transformer 92 is delivered to the terminals 54 and 56 and forms the output waveform 52. The values of the inductance and capacitance of the resonant circuit 90 establish the frequency of oscillations in the resonant circuit 90 and establish the RF output frequency of the output waveform 52. To achieve a sustained output waveform 52, the drive pulses 86 repeatedly charge the resonant circuit 90 with additional energy to replace that energy coupled through the output transformer 92 to the patient. The patterns, timing and sequence of drive pulses 86 applied to the RF power amplifier 60 develop the desired characteristics of the output waveform 52. The functionality of the RF power amplifier 60 in this regard, and the role of the drive pulses 86 in creating the output waveform 52, are well-known.

The power supply control routine 72 establishes the level of the output voltage 94 from the high voltage power supply 62. The voltage from the high voltage power supply 62 is regulated relative to the width of the drive pulses 86 to reduce leakage current by reducing harmonics and to achieve an optimal dynamic range of power control and to achieve faster response in regulating the amount of output power delivered in the output waveform 52, as a result of varying the width of the drive pulses 86. The power supply control routine 72 controls the high voltage power supply 62 to achieve a desired level of the output voltage 94 by supplying a power supply voltage control signal 95. The high voltage power supply 62 responds to the control signal 95 to vary an output voltage 94 delivered to the RF power amplifier 60.

The pattern generation routine 74 uses the pulse width count signal developed by the pulse width control routine 70 and establishes a pattern or sequence for delivering the drive pulses 86 during one drive cycle of the output waveform 52. The pattern of drive pulses 86 varies with each selected mode of operation of the electrosurgical generator 50. There are presently three basic modes of operation of the electrosurgical generator, all of which are established by the characteristics of the output waveform 52. Those modes are a cut mode during which the tissue of the patient 58 is primarily cut, a coagulation mode during which bleeding from the tissue is stopped, and a blend mode during which cutting and coagulation occurs simultaneously. The pattern of drive pulses is varied in each of these different modes to achieve the desired electrosurgical effect on the tissue of the patient. The pattern of pulses created by the pattern generation routine 74 defines the drive pulses 86 of only one mode cycle of the output waveform 52.

The pattern generation routine 74 also adjusts or "dithers" the pattern in a manner which obtains a finer degree of power regulation than is possible from the pulse width control routine 70 adjusting the pulse width count signal itself. The dithering routine of the pattern generation routine 74 adjusts the width of individual pulses within certain drive cycles of each mode cycle. By slightly adjusting the width of only some of the individual pulses of the pattern during each cycle of the output waveform 52, the average power delivered as an average over the entire mode cycle may be regulated to a greater extent than is available from adjusting the width of each drive pulse of that cycle. The dithering routine therefore supplements the basic power regulation capability achieved by executing the pulse width control routine, resulting in more precise average power regulation than is possible from adjusting the pulse width count signal when executing the pulse width control routine.

The pulse generation routine 74 also has the capability of quickly discharging or damping energy from the resonant circuit of the output transformer 92. Damping energy from the resonant circuit 90 before that energy is transferred from the terminals 54 and 56 offers a capability of modifying the characteristics of the output waveform 52 after the drive pulse 86 has transferred the energy to the resonant circuit 90. The pattern generation routine 74 creates the energy damping effect in the resonant circuit 90 by supplying a damping signal 96 to a damping transistor 97 of the RF power amplifier 60. Upon application of the damping signal 96, the damping transistor 97 conducts energy out of the resonant circuit 90. The reduced amount of energy in the resonant circuit causes the oscillations of the output waveform 52 to diminish more rapidly compared to the case where no damping was possible.

The pattern delivery routine 76 utilizes the mode cycle pattern created by the pattern generation routine 74 and repeatedly applies that single mode cycle pattern to create continuing sequences of mode cycles constituting the complete output waveform 52. The pattern delivery routine 76 also converts the digital signals supplied by the pattern generation routine 74 into the actual drive signal 86 which is supplied to the drive transistor 88 of the RF power amplifier 60.

Figure 2:
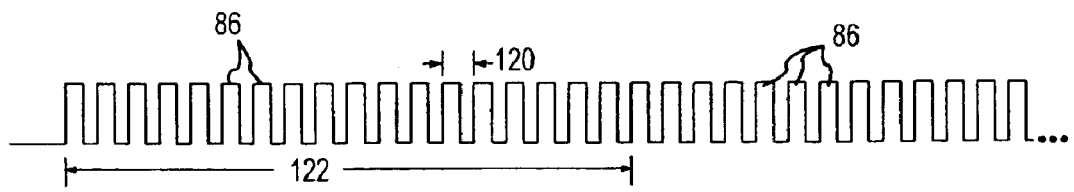
FIG. 2 is a waveform diagram illustrating a pattern of drive pulses applied in mode cycles to an RF output amplifier of the electrosurgical generator shown in FIG. 1, during a cut mode of operation of the electrosurgical generator.
Figure 3:
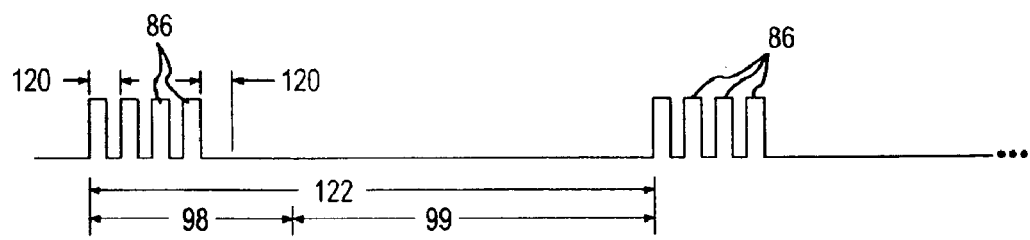
FIG. 3 is a waveform diagram illustrating a pattern of drive pulses applied in mode cycles to the RF output amplifier of the electrosurgical generator shown in FIG. 1, during one type of coagulation mode of operation of the electrosurgical generator.
Figure 4:
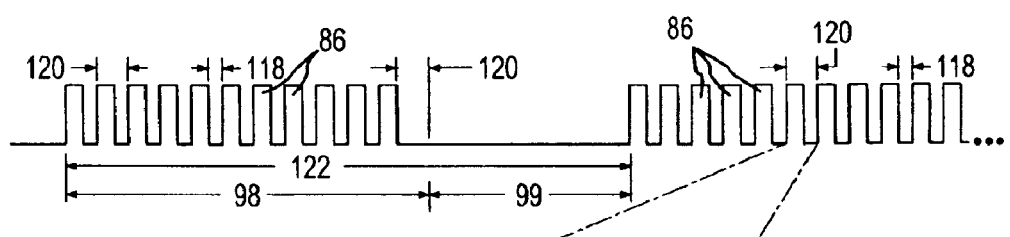
FIG. 4 is a waveform diagram illustrating a pattern of drive pulses applied in mode cycles to the RF output amplifier of the electrosurgical generator shown in FIG. 1, during a blend mode of operation of the electrosurgical generator.

Exemplary output patterns of drive pulses 86 for the cut mode, the coagulation mode and the blend mode are shown in FIGS. 2, 3 and 4, respectively. A continuous uninterrupted sequence of drive pulses 86 defines the cut pattern, as shown in FIG. 2. A repeating duty cycle application of drive pulses 86 defines the coagulation and blend patterns, as shown in FIGS. 3 and 4, respectively. The coagulation pattern of drive pulses 86 shown in FIG. 3 is defined by a relatively short on time 98 during which drive pulses 86 are delivered followed by a relatively long off time 99 during which no drive pulses 86 are delivered. The blend pattern of drive pulses 86 shown in FIG. 4 is defined by a comparatively greater on time 98 of drive pulses and a comparatively shorter off time 99, compared to the coagulation pattern shown in FIG. 3. Other specialized modes of operation exist as subsets of these three basic modes. For example, in "spray" electrosurgical coagulation, a single pulse replaces the multiple pulses shown during the on time 98 shown in FIG. 3. This single spray coagulation drive pulse may have a greater time width than any of the individual drive pulses shown in FIG. 3. The amount of coagulation in the coagulation mode and the relative amounts of cutting and coagulation in the blend mode is varied by adjusting the relative amounts of on time 98 and off time 99. Once the mode is selected, the pattern of drive pulses 86 defined by that selected mode remains unchanged until a different mode is selected.

The mode of operation for the electrosurgical generator 50 is selected from selector input devices 100, as shown in FIG. 1. The desired amount of output power from the output waveform 52 from the selected mode is also selected from the input devices 100. Selecting the mode of electrosurgical operation and the desired output power level generates a mode selection signal 102 and a power selection signal 104. The electrosurgical generator 50 only delivers the RF output waveform 52 when it is activated. A surgeon activates the electrosurgical generator to deliver output electrosurgical power in the output waveform 52 by depressing a switch attached to a handpiece or other electrosurgical instrument, or by stepping on a foot switch. The electrosurgical generator stops delivering the output waveform 52 when the finger or foot switch is opened. In this manner, the electrosurgical generator 50 delivers output power only in response to the assertion of the user-initiated activation signal 108.

The mode selection signal 102, the power selection signal 104, and the user-initiated activation signal 108 are applied to a supervisory processor 106. The supervisory processor 106 interprets the signals 102 and 104, and in response, communicates a power set signal 110 and a mode set signal 112 to the system controller 64. The power set signal 110 is related to the amount of power selected by the user at the input devices 100. The mode set signal 112 is related to the selected mode of operation. Upon receipt of the user-initiated activation signal 108, the supervisory processor 106 delivers a system activation signal 114 to the system controller 64. Asserting the system activation signal 114 causes the system controller 64 to deliver the drive pulses 86 having the characteristics established by the power selection signal 104 and the mode selection signal 102, resulting in the creation and delivery of the output waveform 52.

In response to the mode set signal 112, the pattern generation routine 74 and the pattern delivery routine 76 establish the pattern of drive pulses 86 applied to the RF power amplifier 60, which corresponds to the selected mode of operation, as illustrated by FIGS. 2–4. In response to the power set signal 110, the pulse width control routine 70 and the power supply control routine 72 establish the amount of power in the output waveform 52, by setting and regulating the width of the drive pulses 86 and the output voltage 94 of the high voltage power supply 62. The sampling routine 68 determines the amount of power in the output waveform 52 delivered from the terminals 54 and 56 for use as feedback to the pulse width control routine 70 and the power supply control routine 72 to regulate the power of the output waveform 52 to the level represented by the power set signal 110. This functionality occurs in response to the assertion of the system activation signal 114.

Figure 5:
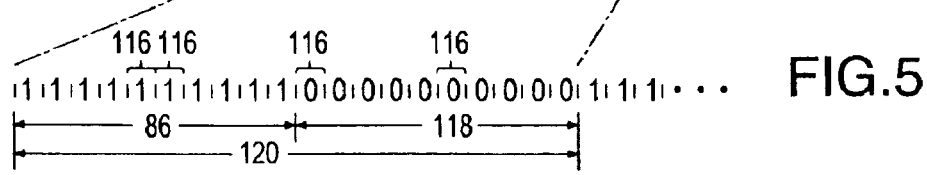
FIG. 5 is an exploded illustration of one drive cycle of the blend waveform diagram shown in FIG. 4, illustrating quantizing time intervals and digital high and low values within each quantizing time interval of that drive cycle which contains one drive pulse.

Because the routines 68, 70, 72, 74 and 76 are executed by processing digital signals, each drive pulse 86, each drive cycle in which a drive pulse 86 occurs, and the pattern of drive pulses 86 which constitute a mode cycle of the output waveform 52 are digitized to be dealt with by the digitally executed routines of the system controller 64. Consequently, each drive pulse 86 and each drive pulse cycle are characterized by quantizing intervals 116, as shown in FIG. 5. Each quantizing intervals 116 represents an equal and uniform segment of time. The width of each drive pulse 86 and each drive cycle 120 is established by a number of quantizing intervals 116. As shown in the example of FIG. 5, the number of quantizing intervals which define each drive cycle 120 is twenty, and the number of quantizing intervals 116 of the drive cycle 120 during which the drive pulse 86 is asserted is ten. The remaining off time portion 118 of each drive cycle 120 of the drive pulses 86 is also defined by a number of quantizing intervals 116, which in the example shown in FIG. 5 is also ten. The time width of each quantizing interval 116 is the same, for example 20 nanoseconds, and is established by the clock (not shown) of the control processor 66 (FIG. 1).

The integral number of quantizing intervals 116 which define the width of the drive pulse 86 is referred to as a "pulse width count" (sometimes abbreviated as "pwCount"). Since the amount of power delivered by the RF power amplifier 60 (FIG. 1) in response to each drive pulse 86 is related directly to the width of the drive pulse 86, the pulse width count also represents the amount of energy delivered by each drive pulse. The power set signal 110 therefore relates to a count number which represents a number of quantizing intervals which the supervisory processor 106 has determined is desired for delivery based on the mode selected.

Figure 6:
FIG. 6 is an illustration of creating one drive pulse from the digital high and low values shown in FIG. 5.

High and low digital logic bits, respectively shown by 1's and 0's in FIG. 5, are inserted in each of the quantizing intervals 116 to represent the presence and absence of the driving pulse 86 during each drive cycle 120. The portion of the drive cycle 120 in which the drive pulse 86 is present is represented by high digital bit values (1's) and off time portion 118 of the drive cycle 120 during which the drive pulse 86 is absent is represented by low digital bit values (0's), as shown in FIG. 6. In the example shown in FIG. 5, the ten high bits (1's) define the width of the drive pulse 86, and the additional low bits (0's) complete each drive cycle 120. The twenty digital bits in sequence establish the time width of the drive cycle 120.

The sequence of bits which define each drive cycle 120 is referred to herein as a "drive cycle word." Establishing the number of bits in each drive cycle word establishes the time width of each drive cycle 120. The pulse width count of high bits (1's) during each drive cycle word establishes the time width of the drive pulse occurring during that drive cycle. It is not necessary that each drive cycle include a drive pulse, and in such circumstances the drive cycle word for that drive cycle will include all 0's. A drive cycle word is not required to use the same number of bits which is typically associated with a conventional digital logic word (16 bits), but can be any number chosen based upon resolution needs.

The time width of each drive cycle 120 is fixed by the supervisory processor 106 in response to the mode set signal 102. In most cases, the time width of each drive cycle 120 is approximately the same for the cut, coagulation and blend modes of operation, as shown in FIGS. 2–4, although the drive cycle for spray coagulation may be substantially different as described above.

Each mode of electrosurgical operation involves sequentially delivering the patterns of drive pulses. Each cycle 122 of the selected electrosurgical mode is referred to herein as a "mode cycle." Each mode cycle 122 is defined by a sequence of drive cycles 120. The cut mode of operation shown in FIG. 2 constitutes a continuous delivery of the drive pulses 86, so the cut mode cycle is defined by any number of drive cycles 120. The coagulation and blend mode cycles 122 shown in FIGS. 3 and 4, respectively, are duty cycle waveforms defined by one on time 98 and one off time 99 in sequence. The on time 98 is defined by a predetermined number of drive cycles 120 in which one drive pulse 86 is delivered during each of multiple drive cycles 120, and the off time 99 is defined by a predetermined number of drive cycles 120 during which a drive pulse is not delivered. Accordingly, by using sequences and patterns of drive cycle words, an entire mode cycle of each selected mode of operation can also be defined.

Figure 7:
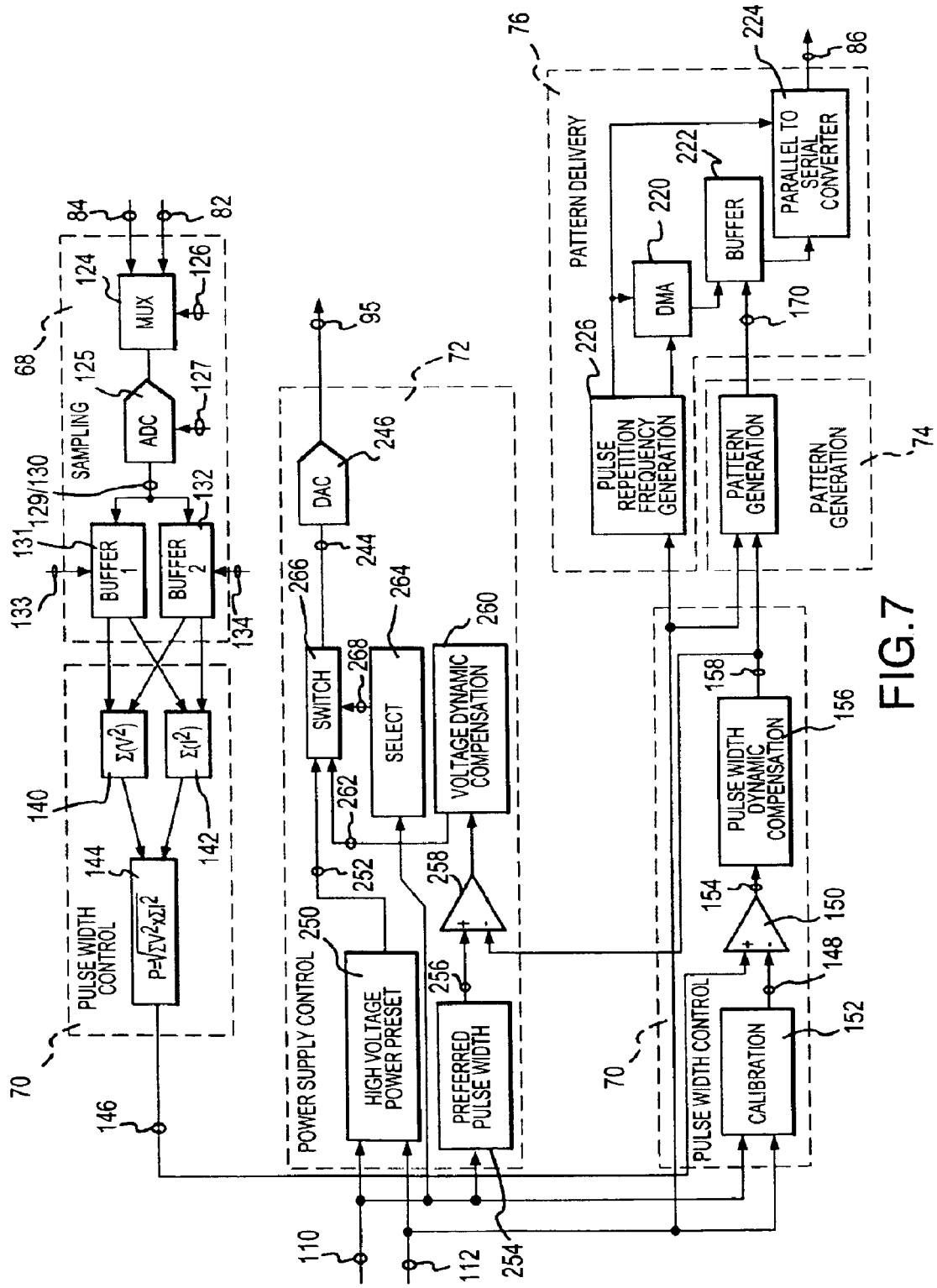
FIG. 7 is a block diagram which illustrates functions or routines performed by a system controller of the, electrosurgical generator shown in FIG. 1, combined with components of hardware with which those routines interact.
Figure 8:
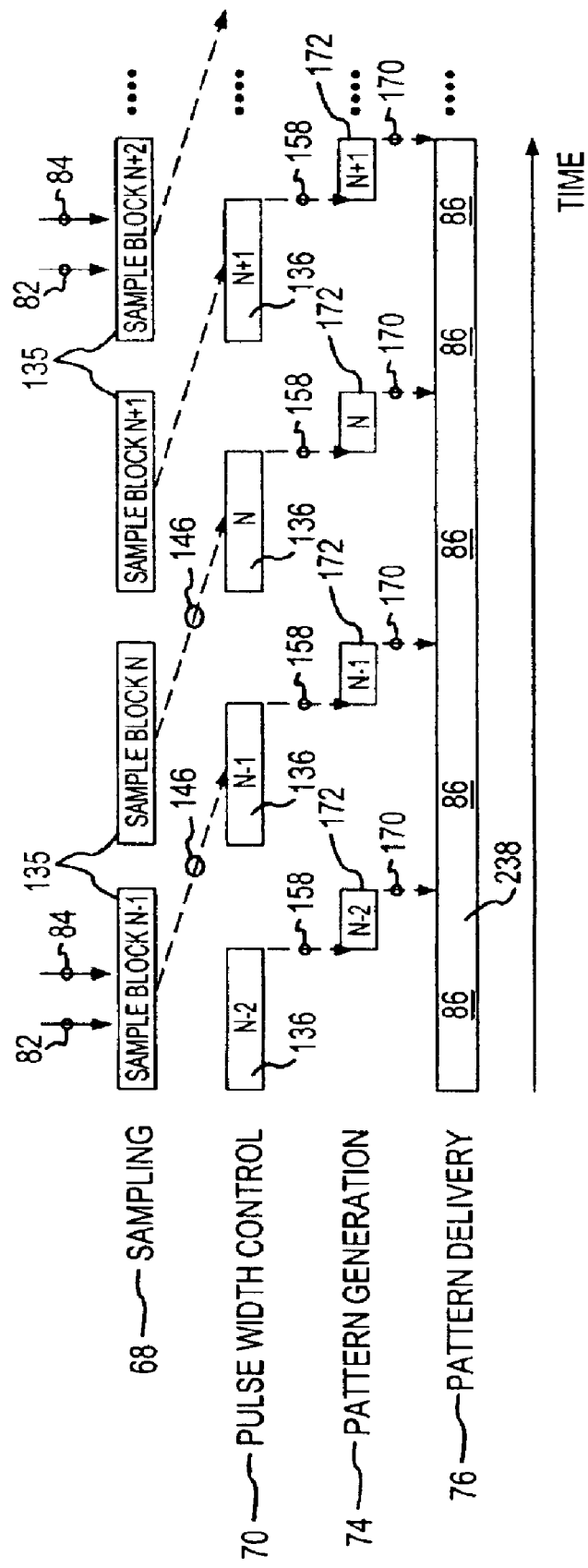
FIG. 8 is a timing and relationship diagram illustrating the relative timing for performing a sampling routine, a pulse width control routine, a pattern generation control routine and a pattern delivery routine executed by a system controller of the electrosurgical generator shown in FIG. 1.

More details concerning the execution of the sampling routine 68, the pulse width control routine 70, the power supply control routine 72, the pattern generation routine 74 and the pattern delivery routine 76, are shown in FIG. 7. The interaction and relationship between the execution of these routines 68, 70, 72, 74 and 76 are generally shown in FIG. 8. The following discussion of the routines 68, 70, 72, 74 and 76 assumes activation of the electrosurgical generator by the delivery of the system activation signal 114 in response to the user-initiated activation signal 108 (FIG. 1). The following discussion is also focused primarily on the ongoing functionality of the electrosurgical generator, after the power set signal 110 and mode set signal 112 have established the power set signal 110 and the mode set signal 112.

The sampling routine 68, shown in FIG. 7, involves the reception of the analog voltage and current feedback signals 82 and 84 from the voltage and current sensors 78 and 80 (FIG. 1), respectively. The analog signals 82 and 84 are applied to a conventional multiplexer (MUX) 124. The MUX 124 applies one of the analog signals 82 or 84 to an analog to digital converter (ADC) 125. The MUX 124 selects one of the signals 82 or 84 to supply to the ADC 125 in response to a selection signal 126. A selection signal 126 is supplied by the sampling routine 68 to cause the MUX 124 to alternate between the signals 82 and 84 when supplying them to the ADC 125. The MUX 124 therefore supplies the analog signal 82 and then the analog signal 84, and then repeats the sequence to alternate between the signals 82 and 84.

The ADC 125 converts the analog value of the signal 82 or 84 which exists at the time when the ADC 125 receives a convert signal 127. The sampling routine 68 delivers the convert signal 127 at a predetermined time after the select signal 126 has been supplied to the MUX 124, to assure that the analog value conducted through the MUX 124 to the ADC 125 has settled to an accurate value. The analog value of the analog signal at the input terminal to the ADC 125 is converted into a corresponding digital form almost immediately in response to the assertion of the convert signal 127. The time at which the convert signal 127 is asserted is a sample point time, and the analog value at the input terminal of the ADC 125 which is converted into its digital value at the sample point time is a sample value.

The action of the MUX 124 and the ADC 125 in supplying the analog voltage and current signals and sampling those analog signals on an alternating basis at sample time points to obtain sample values is shown in FIGS. 9 and 10. FIG. 9 illustrates an exemplary analog voltage feedback signal 82 supplied from the voltage sensor 78 (FIG. 1), and FIG. 10 illustrates an exemplary analog current feedback signal 84 supplied from the current sensor 80 (FIG. 1). At sample time points 128, one of the signals 82 or 84 is converted by the ADC 125 (FIG. 7). Prior to the sample time points 128, the MUX 124 (FIG. 7) has supplied one of the signals 82 or 84 to the ADC 125 (FIG. 7) for conversion. At one sample time point 128, the voltage feedback signal 82 is converted into a voltage sample value 129. At the next sequential sample time point 128, the current feedback signal 84 is converted into a current sample value 130. This alternate conversion of the voltage and current signals 82 and 84 at sequential sample time points 128 results because the MUX 124 alternately applies the signals 82 and 84 to the ADC 125 for conversion in response to the select signal 126 (FIG. 7).

As shown in FIG. 7, the ADC 125 supplies the digital voltage sample values 129 and the digital current sample values 130 in serial form to one of the buffer memories 131 or 132. The buffer memory 131 or 132 to which the ADC 125 supplies the sample values 129 and 130 is designated in response to a select signal 133 or 134. The select signals 133 and 134 are supplied by the sampling routine 68. One select signal 133 or 134 causes one buffer memory 131 or 132 to be filled with the current and voltage sample values during one sampling interval 135, as shown in FIG. 8, and the other select signal causes the other buffer memory to be filled with the current and voltage samples during the next subsequent sampling interval 135. Once one of the buffer memories 131 or 132 has been filled at the conclusion of a sampling interval 135 (FIG. 8), the sampling routine 68 selects the other buffer memory to be filled with the voltage and current sample values 129 and 130 during the next subsequent sampling interval 135 (FIG. 8). As shown in FIG. 8, there is a pause time between each of the sampling intervals 135 executed by the sampling routine 68 (FIG. 7). The values obtained during one sampling interval 135 are referred to as a "block" of sample values.

Figure 11:
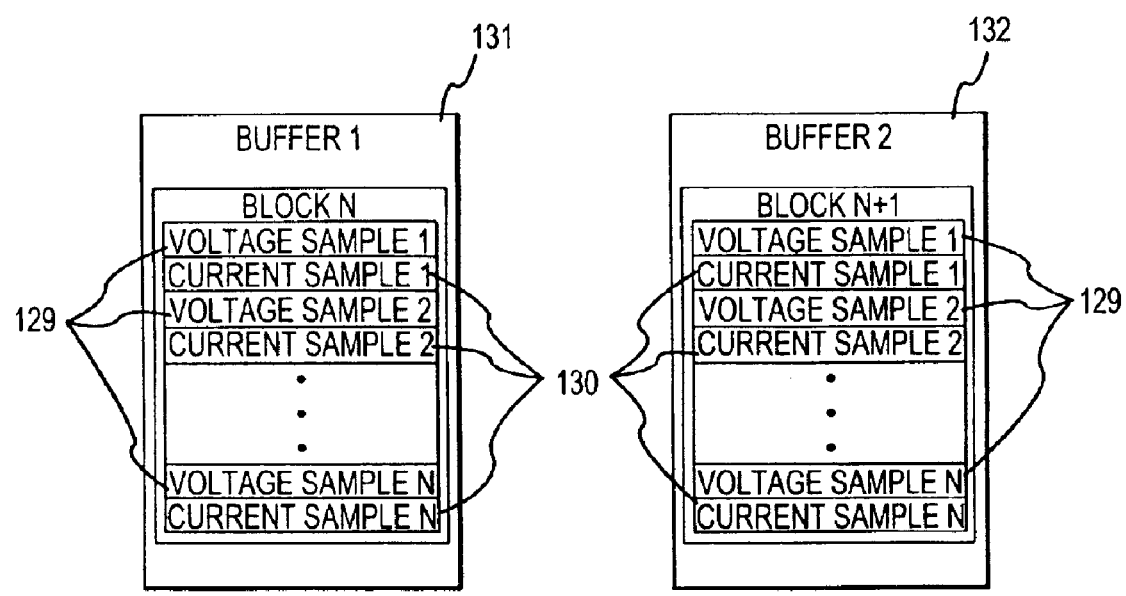
FIG. 11 is a more detailed block diagram of buffer memories used when executing the sampling routine shown in FIG. 6.

The interleaved manner in which the voltage sample values 129 and the current sample values 130 are read into and stored in one of the memory buffers, and the alternating use of the buffers 131 and 132 to store the voltage and current sample values 129 and 130, is illustrated in FIG. 11. Each of the buffer memories 131 and 132 includes direct memory access (DMA) functionality. This DMA functionality allows each buffer memory 131 and 132 to write values sequentially into sequential memory addresses, without the necessity to receive special addressing instructions. The buffer memory 131 therefore writes the first voltage sample value 129 into a first memory location and thereafter writes the first current sample value 130 into the second memory location. Thereafter the second voltage sample value 129 is written into the third memory location and the second current sample value 130 is written into the fourth memory location. This sequence proceeds until all of the desired number of voltage and current sample values have been collected and written into memory locations in the buffer memory 131. This sequence of reading the desired number of voltage and current sample values into a buffer memory is accomplished in one sampling interval 135 shown in FIG. 8. Thereafter the sampling interval 135 terminates, and during the pause time before the commencement of the next sampling interval 135, the sampling routine 68 (FIG. 7) sets up the alternate buffer memory 132 so that it will accept the voltage and current sample values 129 and 130 in sequential memory locations in the same alternating and interleaved manner as occurred with respect to the buffer memory 131.

Using two buffer memories 131 and 132, and reading the current and voltage samples 129 and 130 into the buffer memories 131 and 132 in an alternating manner, allows the sampling to continue almost on a continuous basis, separated only by the pause times between the sampling intervals 135. Consequently, the sampling routine 68 is very effective in collecting enough information to achieve good power regulation in the output waveform 52 (FIG. 1).

The sampling routine 68 causes the sample time points 128 to occur on a regular time or interval basis, but those sample time points 128 are not synchronized with regard to the frequency of the output waveform 52 (FIG. 1). Instead, each sampling interval 135 and the pause time between each sampling interval 135 occurs on a time basis which is independent of the frequency of the output waveform 52.

The number of sample time points 128 which occur during each cycle of the analog voltage feedback signal 82 and the analog current feedback signal 84 (which correspond to cycles of the output waveform 52) is less than the number of samples required under Nyquist theory to generate a completely accurate representation of the signals 82 and 84. Nevertheless, enough information is obtained by sampling at a sub-Nyquist frequency rate to achieve sufficiently accurate output power regulation. Nyquist theory requires that at least two samples be taken during every cycle of a signal in order to accurately represent that signal. Generally speaking, to assure accurate representation, it is usually considered appropriate to take considerably more than two samples of a signal during each of its cycles in order to represent that signal. However, as shown in FIGS. 9 and 10, less than two samples of the analog voltage and current feedback signals 82 and 84 are taken during each cycle of those signals 82 and 84. As discussed herein, this results in no significant loss of effectiveness in achieving very effective output power regulation.

Sampling at a sub-Nyquist rate permits the sampling routine 68 to be executed using components which are less expensive because they function at a lesser rate. Sampling at the sub-Nyquist rate also permits the execution of the sampling routine 68 as described herein, which might be otherwise impossible because of performance limitations on the ADC 125, the MUX 124 and the DMA buffer memories 131 and 132 if the sampling rate was at or greater than the Nyquist rate. These advantages are achieved without sacrificing or compromising the capability of the sampling routine 68 to achieve enough information to accurately represent the average power of the output waveform 52, and to accurately regulate and control the output power. Moreover, because of the relatively autonomous nature in which the voltage and current sample values are obtained, converted and stored, executing the sampling routine 68 does not consume a significant amount of the computational resources of the control processor 66 (FIG. 1), making it possible to devote substantial computational resources to the execution of the other routines.

As shown in FIG. 8, execution of the pulse width control routine 70 commences at 136 after one sampling interval 135 has occurred and a block of sample values has been stored in one of the buffer memories 131 or 132. The timing relationship between the execution of the pulse width control routine 70 and the sampling interval 135 permits using the block of sample values previously obtained in executing the pulse width control routine 70, while another block of sample values is simultaneously being collected. Another advantage to alternating the blocks of sample values collected is that the functionality of the sampling routine 68 does not have to be of such speed and capability to supply data to the pulse width control routine 70 on an immediate basis. Instead, there is little or no significant adverse impact caused by using voltage and current sample values collected during a preceding sampling interval as a basis for regulating and controlling the output power soon thereafter.

Figure 12:
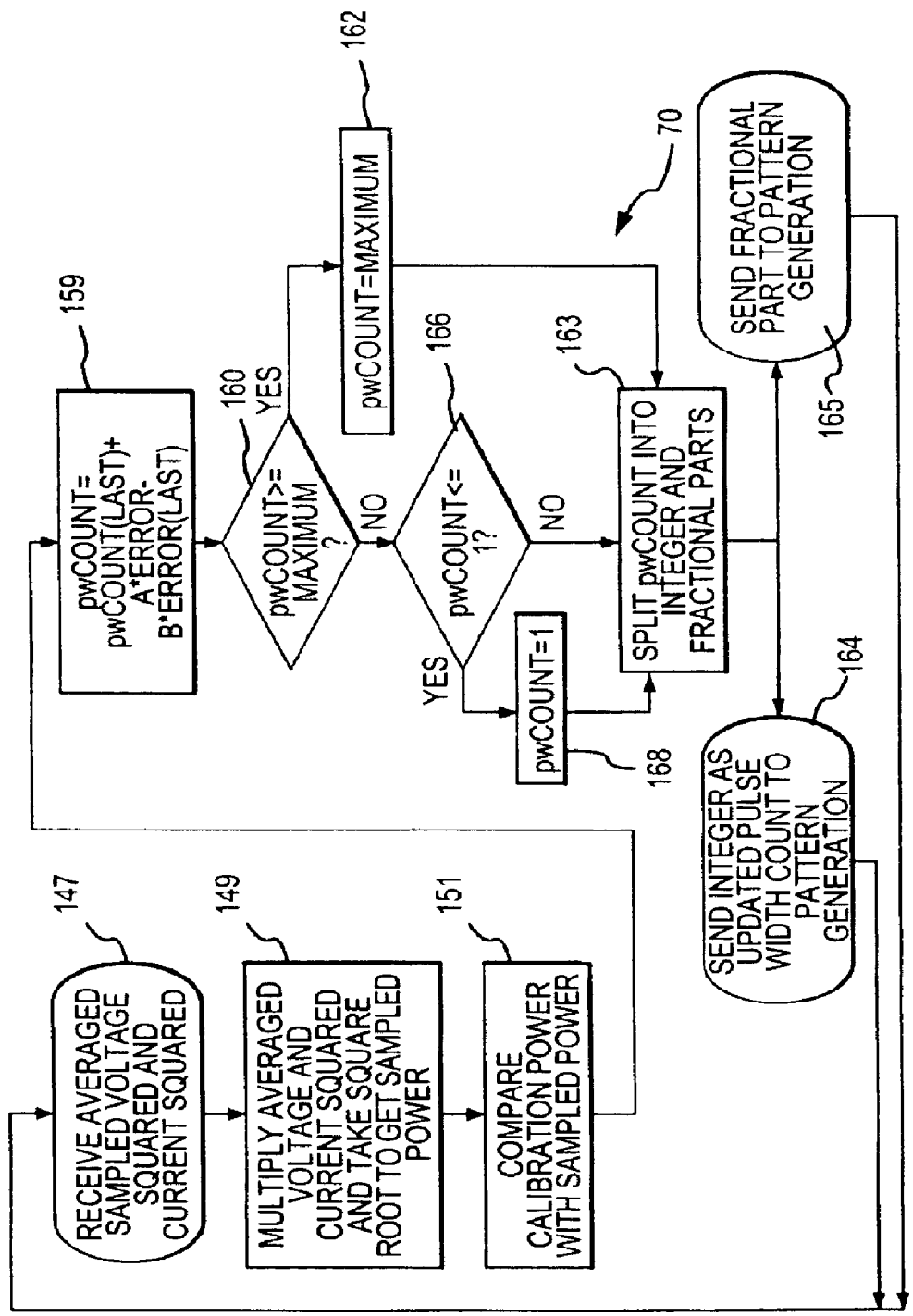
FIG. 12 is a flowchart illustrating functions performed when executing a pulse width control routine shown in FIG. 6.

The pulse width control routine 70 is executed at 136 as shown in FIG. 8, after the completion of the immediate preceding sample block 135. The actual execution of the pulse width control routine 70 is shown in FIGS. 7 and 12. FIG. 12 shows one execution of the pulse width control routine 70.

As shown in FIG. 7, after all of the voltage and current signal samples have been collected and stored in one of the buffer memories 131 or 132, each of the voltage sample values is squared and then all of the squared voltage values are summed, as shown by the calculation 140. In a similar manner, each of the current sample values is squared and then all of the squared current values are summed, as shown by the calculation 142. Summing all of the squared values together develops a value which is related to the average of the squared values. Although the number of current and voltage sample values is not divided into the sum of all of the squared values achieved by performing the calculations 140 and 142, the number of samples collected in each sampling block is the same, so the result of the addition of the squared sample values is itself a value which represents the average of the squared values. These summed squared sample values are then multiplied together and the square root of this product is then taken as shown by the calculation 144. The outcome from executing these calculations 144, 142 and 140 is a sampled block average power signal 146 which represents the root mean square (RMS) of the average power delivered over the time period during which the block of sample values stored in the buffer memory 131 or 132 was collected (135, FIG. 8).

Steps 147 and 149 of the pulse width control routine program flow shown in FIG. 12 illustrate the execution of the steps represented by the calculations 140, 142 and 144 shown in FIG. 7. At step 147, the averaged squared voltage sample values and the averaged squared current sample values obtained from performing the calculations 140 and 142 (FIG. 7) are received. Thereafter, those averaged squared sample values are multiplied together, and the square root of the product is taken, as shown at step 149. The result of the step 149 is the sample block average power signal 146 (FIG. 7).

As shown in FIG. 7, the sample block average power signal 146 is compared to a calibrated power signal 148 in a comparing function 150. The calibrated power signal 148 is generated by a calibration subroutine 152 in response to the power set signal 110 and the mode set signal 112. Based on the selected mode as indicated by the mode set signal 112 and previous empirically determined information concerning the performance of the particular electrosurgical generator 50 (FIG. 1), the calibration subroutine 152 adjusts the power set signal 110 to correlate the actual output power of the output waveform 52 to the amount of output power selected at the input devices 100 and represented by the power set signal 104. The calibration subroutine 152 therefore provides the ability to adjust each particular electrosurgical generator so that it will deliver exactly the amount of output power selected by the user.

The sample block average power signal 146 and the calibrated power signal 148 are compared in a comparing function 150, which is also illustrated at step 151 in FIG. 12. If there is a difference or error between the sample block average power signal 146 and the calibrated power signal 148, a power error signal 154 is created and supplied to a pulse width dynamic compensation subroutine 156. The pulse width dynamic compensation subroutine 156 responds to the amount of the power error signal 154 by adjusting the pulse width count signal (pwCount) which had been used previously to establish the width of the driving pulses 86. The pulse width dynamic compensation subroutine 156 adjusts the previous pulse width count signal to create an updated pulse width count signal 158. The updated pulse width count signal 158 therefore represents an adjustment to the previous pulse width count signal to adjust the output power created by the drive pulses 86 in the output waveform 52 (FIG. 1) to a value which is closer to or coincident with the value represented by the power selection signal 104 (FIG. 1). The updated pulse width count signal is used to control the width of each driving pulse until the next execution (136, FIG. 8) of the pulse width control routine 70.

During continued operation of the electrosurgical generator, the previous pulse width count signal is that pulse width count signal which existed as a result of the immediately preceding execution 136 (FIG. 8) of the pulse width control routine 70. Upon initially activating the generator, there will be no previous pulse width count signal, and in that case, the previous pulse width count signal can be one of two different values. In one case, the previous pulse width count signal can be zero, which will require a number of executions (136, FIG. 8) of the pulse width control routine 70 in order to build the value of the pulse width count signal up to the desired level. In the other case, the supervisory processor 106 (FIG. 1) may calculate a starting value for the pulse width count signal and supply the starting value pulse width count signal to the pulse width dynamic compensation subroutine 156 for use. The calculated starting value for the pulse width count signal is based on the user-selected mode of operation and the user-selected power, represented by the signals 102 and 104 (FIG. 1).

The performance of the pulse width dynamic compensation subroutine 156 is illustrated in FIG. 12. At step 159, an adjusted pulse width count signal is determined. The adjusted pulse width count signal, determined at step 159, is established by the previous pulse width count signal (pwCount(last)) to which there is added a value equal to the current error determined by the comparing function 150 (FIG. 7) and the comparing step 151 multiplied by a constant value (A). From that value, the value of the previous error (error (last)) multiplied by another constant (B) is subtracted. The previous pulse width count signal and the previous error are those values which were established during the previous execution (136, FIG. 8) of the pulse width control routine 70. Thus, the currently established pulse width count value and the current error become the previously established pulse width count value and the previously established error, respectively, upon the next subsequent execution of the pulse width control routine 70. The currently established pulse width count value and the current error are held in memory until they are used in the subsequent execution of the pulse width control routine 70. The constants A and B are analytically and empirically established based on control theory to obtain the desired response.

The result of performing the calculation at step 159 is the adjusted pulse width count signal. In most circumstances, the value of the adjusted pulse width count signal will not be an even integer value, because of the variable nature of the error determined by the comparing function 150 (FIG. 7) as well as the previous error. The adjusted pulse width count signal is compared at step 160 to a predetermined maximum pulse width count value. The predetermined maximum pulse width count value is that value which corresponds to the maximum width permitted for the drive pulse 86. If the drive pulse 86 exceeds a value related to the type of output transformer 92 (FIG. 1), the magnetic characteristics of the output transformer will saturate and result in possible damage to the RF output amplifier 60 (FIG. 1). The ability to regulate power effectively by controlling the width of the drive pulses 86 is also diminished if those pulses increase in time width beyond a predetermined limit. Although the predetermined maximum time width of the drive pulses 86 may vary depending upon the characteristics of the output transformer and the RF output amplifier, the maximum predetermined time width will generally be less than approximately 50 percent of the time width of the drive cycle in which the drive pulse 86 appears.

If the adjusted pulse width count signal is greater than the predetermined maximum pulse width count value, as determined at step 160, the adjusted pulse width count signal is set equal to a predetermined maximum pulse width count value at step 162. The predetermined maximum pulse width count value set at step 162 is thereafter evaluated at step 163 to determine whether the value has a fractional part. Because the predetermined maximum pulse width count value set at step 162 is an integral value, the adjusted pulse width count signal with the predetermined maximum pulse width count value therefore becomes the updated pulse width count signal which is sent to the pattern generation routine 74 (FIG. 7) at step 164. In the case of the predetermined maximum pulse width count value set at step 162 being an integral value, there will be no fractional part to send at step 165 (or the fractional value to be sent will be zero).

If the comparison at step 160 indicates that the adjusted pulse width count signal is less than the predetermined maximum pulse width count value, a further determination is made at step 166. If the determination at step 166 is that the adjusted pulse width count signal is less than the value one, with the one being the minimum acceptable value for the adjusted and updated pulse width count signal, the adjusted pulse width count signal is set to one at step 168. The value one set at step 168 is evaluated at step 163. Because the value one is an integral value, the value one becomes the updated pulse width count signal, and it is supplied to the pattern generation routine 74 (FIG. 7) at step 164. The value one has no fractional part so there will be no fractional part to send at step 165.

A pulse width count signal which is equal to one is practically too narrow to create any output power in the output waveform 52 (FIG. 1). Instead, by establishing the updated pulse width count signal that the smallest value possible, i.e. one, a signal is created which can be recognized by monitoring the functionality in the electrosurgical generator to indicate that the electrosurgical generator is performing in accordance with the selected mode of operation. More details concerning this functionality are described in the above-mentioned U.S. patent application for an Electrosurgical Generator and Method for Cross-Checking Mode Functionality.

If the result of the determination at 166 is negative, indicating that the adjusted pulse width count signal is greater than one, the adjusted pulse width count signal is evaluated at step 163. Because the value established at step 159 is more probable to be a non-integral value, the evaluation at step 163 results in the integral value being supplied as the updated pulse width count signal at step 164. The fractional value is also supplied at step 165 to the pattern generation routine 74. As an example of this functionality, assume that the adjusted pulse width count signal was 8.25. The value 8 is the integral value, and the fractional part is 0.25. In this example, the updated pulse width count signal sent at step 164 is the value 8, and the fractional part which is sent at step 165 is the value 0.25. As will be discussed in conjunction with the pattern generation routine 74, use of the fractional part sent at step 165 provides the ability to obtain a finer granularity in power regulation than is possible by using the updated pulse width count signal itself.

After the updated pulse width count signal is supplied from step 164 to the pattern generation routine 74 (FIG. 7), the program flow associated with the pulse width control routine 70 loops from steps 164 and 165 to step 147. Thereafter, the pulse width control routine 70 is ready to commence its next execution (136, FIG. 8), in response to the collection of the next sample block of voltage and current sample values.

The execution (136, FIG. 8) of the pulse width control routine 70 proceeds without reliance on attaining continual information from other routines of the electrosurgical generator, based only on the sample block average power signal 146 and the previous pulse width count signal and the previous error. Executing the pulse width control routine 70 promotes the calculation of power regulation information on a rapid and continuous basis, by the substantially unrestricted use of the control processor 66 of the system controller 64 (FIG. 1).

As shown in FIG. 7, the pattern generation routine 74 responds to the updated pulse width count signal 158 and the mode set signal 112 to establish one mode cycle 122 (FIGS. 2–4). The pattern generation routine 74 therefore creates and supplies enough drive cycle words 120 (FIG. 5) to form one mode cycle 122 (FIG. 4). The signals constituting one mode cycle are supplied to the pattern delivery routine 74. The mode cycle signal 170 therefore represents the pattern of drive pulses with the appropriate energy content to be delivered during one mode cycle 122 (FIG. 5). The mode cycle signal 170 constitutes a series of drive cycle words 120 (FIG. 5), and each of the drive cycle words 120 constitutes a series of digital high and low bit values (1's and 0's).

Each execution 172 of the pattern generation routine 74 shown in FIG. 8 occurs in response to the execution of the pulse width control routine 70. As shown in FIG. 8, the pattern generation routine 74 consumes relatively few computational resources of the control processor 66 of the system controller 64 (FIG. 1), as indicated by the time involved in the execution 172, but those resources are consumed after the pulse width control routine 70 has been executed at 136. Execution 172 of the pattern generation routine 74 also proceeds autonomously, based only on the mode select signal 112 and the updated pulse width count signal 158 (FIG. 7).

Figure 13:
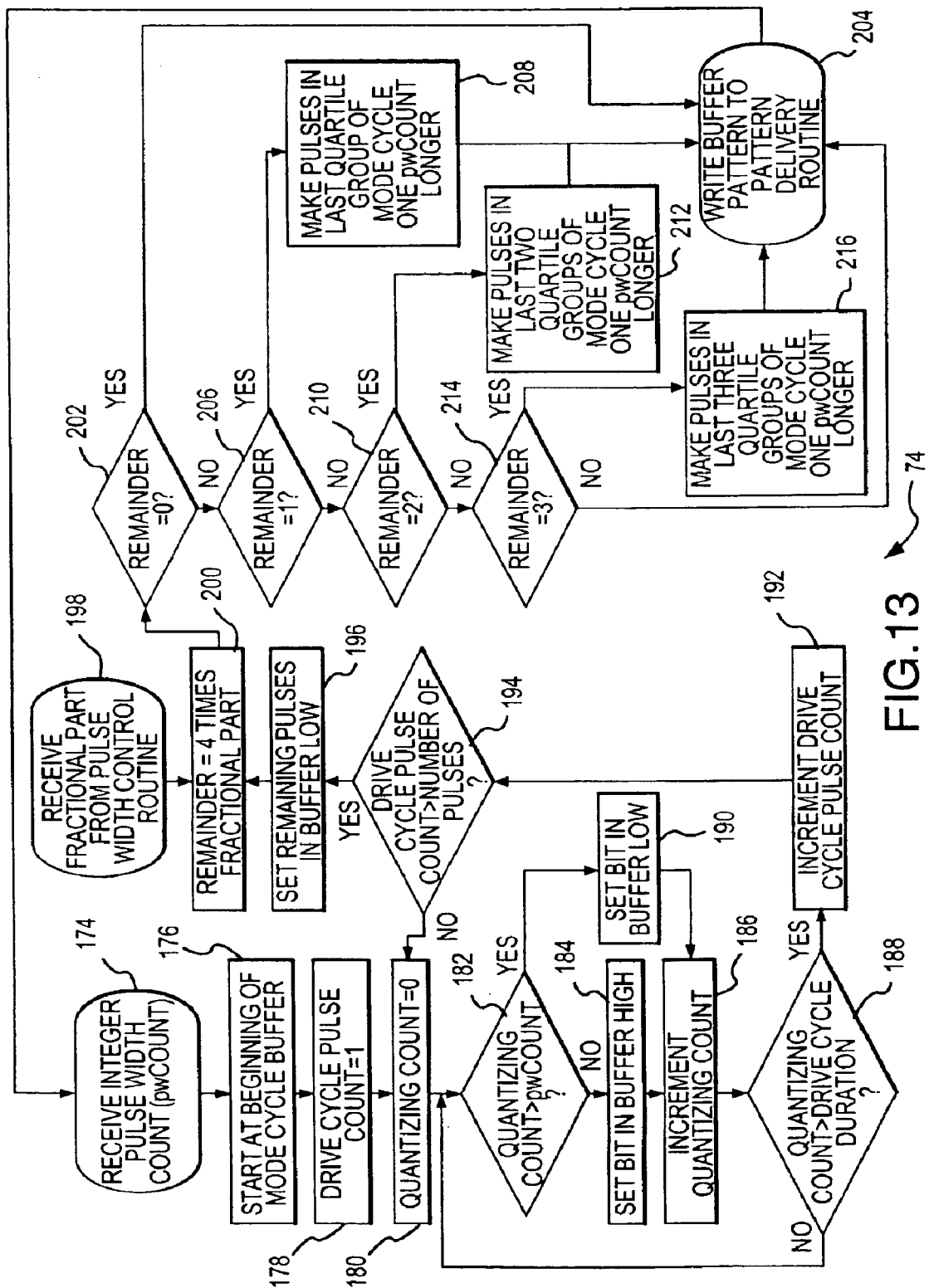
FIG. 13 is a flowchart illustrating functions performed when executing a pattern generation routine shown in FIG. 6.

The manner in which the pattern generation routine 74 executes is shown in FIG. 13. The updated pulse width count signal (pwCount) 158 (FIGS. 7 and 12) is received at step 174. At step 176, reference is made to a mode cycle buffer having a length capable of receiving all of the digital bit values used to define one complete mode cycle 122 of the output waveform 52 (FIG. 1) for the selected mode of operation. The length of the mode cycle buffer is established by the mode select signal 112 (FIG. 7). At step 178, a drive cycle pulse count value is established as equal to one. The drive cycle pulse count refers to a pointer to each drive pulse 86 which is to be created in the mode cycle 122 in accordance with the selected mode (FIGS. 2–4). As an example of the pulses and each mode cycle, four drive pulses 86 are present in each mode cycle 122 shown in FIG. 3, and eleven drive pulses 86 are present in each mode cycle 122 shown in FIG. 4. The function of the drive cycle pulse count value is to point to each of those drive pulses 86 in the sequence in which they appear in the mode cycle. At step 180 shown in FIG. 13, a quantizing count is set equal to 0. The quantizing count refers to a pointer to each of the quantizing intervals 116 (FIG. 5) in which a digital high bit (1) or a digital low bit (0) will be placed to define each drive cycle 120 (FIG. 5). As an example of the bits in each drive cycle, high bits (1's) are placed in the first through the tenth quantizing intervals 116 in FIG. 5 and low bits (0's) are placed in the eleventh through twentieth quantizing intervals.

At step 182 shown in FIG. 13, a determination is made whether the quantizing count is greater than the updated pulse width count signal. Since the value established for the quantizing count value at step 180 is 0, the determination at step 182 is negative. Thereafter, at step 184, a high bit (1) is set into the first memory bit location of the buffer. In the example shown in FIG. 5, step 184 (FIG. 13) is represented by the insertion of the first high bit (one) in the first quantizing interval 116. Following the execution of step 184 shown in FIG. 13, the quantizing count is incremented at step 186. Incrementing the quantizing count value at step 186 has the effect of referring to the next quantizing interval, which in the example shown in FIG. 5 constitutes the second quantizing interval 116 in which a high bit (one) is located. Next, at step 188 shown in FIG. 13, a determination is made whether the quantizing count is greater than the drive cycle duration. The drive cycle duration is that number of quantizing intervals which define one entire drive cycle in which a drive pulse 86 will be generated. In the example shown in FIG. 5, the drive cycle duration is twenty quantizing intervals 116.

The steps 182, 184, 186 and 188 will execute in the manner described until high bits (1's) have been placed in each of the quantizing intervals which are equal in number to the pulse width count signal. Thus, the repeated execution of the steps 182, 184, 186 and 188 in that sequence will occur until the high digital bits define the time width of the drive pulse 86. In the example shown in FIG. 5, the execution of the steps 182, 184, 186 and 188 will occur ten times, with each execution of those steps placing an additional high bit (1) in the next sequential quantizing interval 116.

After all of the high bit values have been placed in the quantizing intervals to define the width of the drive pulse 86 by execution of the steps 182, 184, 186 and 188 in the manner described, the next determination at step 182 will be affirmative. The affirmative determination results because the quantizing count is now one greater (as a result of step 186) than the number of high bit values which define the width of the drive pulse.

The affirmative determination at step 182 results in setting a low bit (0) in the next buffer position which corresponds to the next quantizing interval, at step 190. In the example shown in FIG. 5, execution of the step 190 results in setting the first low bit (0) in the eleventh quantizing interval. After execution of the step 190, shown in FIG. 13, the program flow again increments the quantizing count at step 186 and then proceeds to the determination at 188. Because the number of quantizing intervals necessary to define a drive cycle 120 (FIG. 5) has not yet been exceeded as determined at step 188, the program flow reverts back to the determination at step 182.

The determination at step 182 is again affirmative, resulting in another low bit (0) being placed in the next quantizing interval at step 190, followed by incrementing the quantizing count at step 186 again, and arriving at a negative determination at step 188. The steps 182, 190, 186, 188 are repeatedly executed in this sequence until the determination at step 188 indicates that the quantizing count is greater than the total number of quantizing intervals in a drive cycle. By reaching this point in the program flow, the remaining low bits (0's) will have been placed in the remaining quantizing intervals 116 which constitute the off time 118, thus completing one drive cycle as exemplified in FIG. 5.

An affirmative determination at step 188 increments the drive cycle pulse count at step 192. Incrementing the drive cycle pulse count refers to the second drive cycle in the mode cycle. The next determination at step 194 determines whether the number of drive pulses in the entire mode cycle have been generated. Because only one drive cycle has been generated by executing the steps 182, 184, 186, 188 and 190, and because the required number of drive pulses in the entire mode cycle has not been generated, the program flow moves from step 194 to step 180. The total number of drive pulses in the entire mode cycle is known from the mode set signal 112 (FIG. 1).

Moving from step 194 to step 180 starts again the previously described process of generating the high and low bit values necessary to define the drive pulse 86 and the off time 118 in the second drive cycle of the mode cycle. Once the definition of the second drive cycle has been completed in the same manner as previously described, the determination at step 194 causes this program flow to repeat until all of the drive cycles that contain drive pulses 86 have been defined. In the example shown in FIG. 3, four drive cycles will have been defined to complete the on time 98 of the mode cycle 122. In the example shown in FIG. 4, eleven drive cycles will have been defined to complete the on time 98 of the mode cycle 122.

Once execution of the step 194 shown in FIG. 13 results in an affirmative determination, the program flow moves to step 196. In step 196 low bits (0's) are set into all of the remaining buffer bit locations which correspond to the quantizing intervals of the off time of the mode cycle. In the examples shown in FIGS. 3 and 4, enough low bits (0's) are set to define the off times 99 of those mode cycles 122. This situation also assumes that the drive pulses appear at the beginning part of each drive cycle. If this is not the case, the program flow as described can be adapted to placed the drive pulses at the desired locations within the mode cycle.

Execution of the step 196 therefore completes the basic definition of the mode cycle using the updated pulse width count value obtained at step 174 from executing the pulse width control routine 70 shown in FIG. 12. The mode cycle buffer is filled with high and low bit values which define the pattern of drive pulses necessary to constitute an entire mode cycle, and the width of the drive pulses is established at a value to regulate the output power based on the updated pulse count value obtained from executing the pulse width control routine 70 (FIGS. 7 and 12). This pattern of high and low bit values in the mode cycle buffer which defines the basic entire mode cycle would constitute the mode cycle signal 170 supplied to the pattern delivery routine 76, except for the fact that a finer degree of power regulation will usually be required from the entire mode cycle. A finer degree of regulation is indicated by the fractional part of the calculation of the updated pulse width count at step 165 in the pulse width control routine 70, shown in FIG. 12. The fact that the fractional part exists indicates that the integer value of the drive pulses established does not exactly achieve the power regulation required by calculating the adjusted pulse width count at step 159 (FIG. 12). Accordingly, the remaining portion of the pulse generation routine 74, beginning at step 198, involves dithering to achieve that finer degree of power regulation by adjusting the width of some but not all of the drive pulses in the entire mode cycle.

At step 198, the fractional part determined at step 165 in the pulse width control routine 70 (FIG. 12) is supplied to the pattern generation routine 74. The fractional part received at step 198 is used in a calculation to determine a remainder value, at step 200. The remainder value is calculated by multiplying the fractional part by 4, and rounding the resulting product number down to the nearest integer value. In the example previously discussed in connection with the pulse width control routine 70 (FIG. 12), the fractional part was 0.25. Therefore, executing the step 200 involves multiplying 0.25 by four and arriving at a remainder value of one. This remainder value is thereafter used to determine whether any additional high bits (1's) will be inserted to increase the width of any of the drive pulses in the entire mode cycle established by previously executing steps 176 to 196 as shown in FIG. 13.

If the remainder obtained at step 200 is 0, as determined at 202, there is an indication that the width of the drive pulses established by the updated pulse width count signal 158 (FIG. 7) is the best available value for the power regulation until the next execution of the pulse width control routine 74 results in a different value of the updated pulse width count and fractional value. In this case, the affirmative determination at step 202 results in the delivery of the pattern of high and low bits in the buffer which constitute the mode cycle signal 170 to the pattern delivery routine 76 (FIG. 7), as shown at step 204. The pattern of high and low bits which is delivered at step 204 as the mode cycle signal (170, FIG. 7) define the entire mode cycle 122 formed by the series of individual drive cycles 120.

If the remainder obtained at step 200 is not zero, the determination at 202 is negative and the program flow proceeds to the determination at 206. An affirmative determination at 206 results in increasing the width of the drive pulses defined by the last quartile group of drive pulses of the mode cycle by an extra high bit (1), as shown at step 208. In other words, by reference to the example shown in FIG. 5, the first low bit (0) of the off time 118 following the last high bit (1) which define the drive pulse 86 will be substituted with a high bit (1). This substitution then changes the width of the drive pulse 86 to eleven quantizing intervals 116 rather than ten, and changes the width of the off time 118 from ten quantizing intervals 116 to nine. This adjustment is made within all of the drive cycles 120 in the last quartile of the total number of drive cycles in which a drive pulse is present. The drive cycle pulse count is determined from the mode said signal 112 (FIG. 1).

As an example of this functionality by reference to FIG. 4, there are eleven drive cycles 120 which contain a drive pulse 86. The last quartile of those eleven drive cycles would be formed by the tenth and eleventh drive cycles. In that circumstance, the width of the drive pulses in the tenth and eleventh drive cycles would be increased by one pulse width count, in the manner described. This has the effect of delivering more power over the average of the entire mode cycle than would otherwise be delivered if the width of the drive pulses during the entire mode cycle remained set at the basic value established by the updated pulse width count signal received at step 174. By increasing only a few of the drive pulses in a quartile of the entire number of drive pulses delivered during the mode cycle, a slightly increased amount of energy is delivered than would be possible by adjusting the width of all of the drive pulses by a complete increment.

For example, if the mode cycle shown in FIG. 4 had twelve drive cycles in which there were drive pulses rather than the eleven as shown, the effect of increasing the width of the three drive pulses in the last three drive cycles would be the same as forming each of the drive pulses by an ¼ value of the pulse width count signal. Since the updated pulse width count signal 158 must be an integer value, and fractional portions of the pulse width count signal cannot be used to form drive signals, this "dithering" modification based on the entire mode cycle achieves the same effect on an average throughout the entire mode cycle. In other words, this dithering compensates for the fractional error which could not be accounted for by the integer value of the updated pulse width count, during the execution of the pulse width control routine 70. In the exemplary mode shown in FIG. 4, only two of the drive cycles would receive an extra increment of pulse width count, so the average amount distributed over the eleven drive pulses would not constitute an increase in average power delivered by ¼, but instead would amount to only an increase of ²⁄₁₁. Nevertheless, the slight difference under those circumstances where the number of drive pulses in the mode cycle is not exactly divisible by four still achieves a finer regulation in output power than is possible by relying only on the integer values of the updated pulse width count signal for establishing the widths of the drive pulses. Once the width of the drive pulses in the last quartile of the drive cycles which contain drive pulses is increased by one pulse width count, as shown at step 206 in FIG. 13, the buffer pattern is written to the pattern delivery routine as the mode cycle signal 170 (FIG. 7).

If the determination at 205 is negative, the program flow proceeds to the determination at 210, where the remainder is determined to be equal to two. An affirmative determination at step 210 results in increasing the pulse width of the drive pulses in the last two quartiles of drive cycles having drive pulses in the mode cycle, as shown at step 212. Thereafter the pattern of high bits and low bits which define the entire mode cycle are delivered to the pattern delivery routine 76 as the mode cycle signal 170 (FIG. 7) at step 204. The width of the drive pulses increased in the last two quartiles which occurs at step 212, proceeds in the same manner as described with respect to step 208, except that more drive pulses are increased in width. The effect of increasing the drive pulses in the last two quartiles is to increase the average power delivered during the entire mode cycle by one-half the amount that could be achieved by changing all of the drive pulses that constitute that mode cycle by one integer pulse width count.

If the determination at step 210 is negative, the determination at step 214 is thereafter performed. An affirmative determination at step 214 results in increasing the pulse width of the drive pulses in the last three quartiles of the drive cycles having drive pulses in the drive mode by one integer pulse width, as shown at step 216. Thereafter, the pattern of high and low bits in the buffer which constitute the entire mode cycle are delivered to the pattern delivery routine at 204. The effect of performing step 216 is to increase the average pulse width of all of the drive pulses of the mode cycle by ¾ of one integer pulse width count.

The dithering achieved by performing steps 200, 202, 206, 208, 210, 212, 214 and 216 is effective on a mode cycle-by-mode cycle basis, and is repeated with each subsequent mode cycle so that the average power delivered over a series of mode cycles can therefore be regulated very precisely. An equally effective alternative to using the fractional part established at step 165 (FIG. 12) as a basis for the dithering at step 200 (FIG. 13) is to start with a value representing the entire energy content of all of the drive pulses during an entire mode cycle, and then divide that value by the number of drive pulses in the mode cycle. The remainder value of such division is then used as the basis for the dithering. Although the scale of the values is different in this alternative technique compared to the technique described in detail herein, the effect is essentially the same.

As shown in FIG. 8, the pattern generation routine 74 is executed at 172 after the pulse width control routine 136 has been executed, but within the time frame of each sample block 135. Because the execution of the pulse width control routine 136 has terminated, the computational resources to perform the pattern generation routine 74 are not diminished because of other demands for significant computational resources of the control processor 66 (FIG. 1).

Referring to FIG. 7, the pattern delivery routine 76 utilizes the bit values of the mode cycle signal 170 supplied by the pattern generation routine 74 at step 204 (FIG. 13) to create and continue the electrosurgical output waveform 52 for as long as the electrosurgical generator is activated. This functionality consists of repeatedly delivering the bit patterns of the mode cycle signal 170 until the mode cycle signal 170 is updated or the activation of the electrosurgical generator ceases by the de-assertion of the user-initiated activation signal 104 (FIG. 1). An updated mode cycle signal 170 is created when execution of the pulse width control routine 74 results in a different value of the mode cycle signal. Selecting a different mode of operating the electrosurgical generator will also result in a different mode cycle signal 170, although the electrosurgical generator is not activated when mode selections are made.

The pattern delivery routine 76 makes use of a DMA controller 220, a buffer memory 222, and a parallel to serial converter 224 to create the drive pulses 86 from the mode cycle signal 170. The mode cycle signal 170, with its patterns of 1's and 0's which define the multiple drive cycle words 120 that constitute one entire mode cycle 122 (FIG. 4), is written to the buffer memory 222 as a series of conventional digital logic bytes. The DMA controller 220 is controlled by instructions from the pattern delivery routine 76 and by a pulse repetition frequency generation subroutine 226. The pulse repetition frequency generation subroutine 226 establishes the frequency at which the mode cycle signals 170 stored in the buffer memory 222 are delivered and converted to create the drive pulses 86 in accordance with the selected mode of operation indicated by the mode set signal 112. Of course, the frequency at which the mode cycle signals 170 are delivered establishes the frequency at which the drive pulses 86 are delivered to the resonant circuit 90 of the RF power amplifier 60 (FIG. 1).

The DMA controller 220 causes the buffer memory 222 to continually deliver the bytes in the sequence which define the mode cycle signal 170. The parallel to serial converter 224 converts the 1's and 0's of each delivered byte into the analog drive pulses 86. This conversion is illustrated in FIGS. 5 and 6. During each quantizing interval 116 in which a high bit (1) is present, the parallel to serial converter 224 establishes a high level of the drive pulse 86. In those quantizing intervals 116 in which a low bit (0) is present, the parallel to serial converter 224 establishes a low level during the off time portion 118 of the drive cycle 120. In this manner, the serial to parallel converter 224 creates the drive pulses 86 and the pattern of drive pulses within one mode cycle from the high and low bits of the mode cycle signal 170 stored in the buffer memory 222.

Once one complete mode cycle signal has been converted by the parallel to serial converter 224, the DMA controller 220 repeats the process by again delivering the bytes which define the mode cycle signal 170 to the parallel to serial converter for conversion. This repeated process of delivering and converting the mode cycle signal 170 occurs until the electrosurgical generator is no longer activated.

Figure 14:
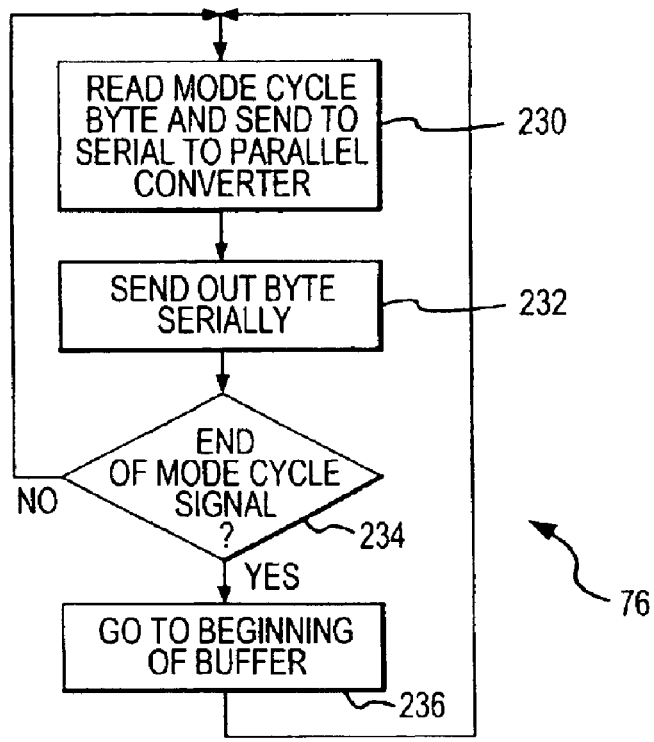
FIG. 14 is a flowchart illustrating functions performed when executing a pattern delivery routine shown in FIG. 6.

The process flow of executing the pattern delivery routine 76 is illustrated in FIG. 14. At step 230, one byte of the mode cycle signal 170 (FIG. 7) is read from the buffer memory 222 (FIG. 7) and is sent for conversion to the parallel to serial converter 224 (FIG. 7). The parallel to serial converter 224 converts the bits of the byte to the serial form illustrated in FIG. 6, at the step 232 shown in FIG. 14. After each byte which has been read and converted at step 232, a determination is made at step 234 of whether the byte read and converted is the last byte of the mode cycle signal 170 (FIG. 7). A negative determination at step 234 results in a loop back where the DMA controller 220 supplies the next byte in the mode cycle signal so that steps 230 and 232 can be again executed. When all of the bytes which define the mode cycle signal 170 (FIG. 7) have been read from the buffer memory 222, as indicated by an affirmative determination at step 234, the entire mode cycle signal is again used for delivery of the drive pulses 86 and the patterns of drive pulses by the step 236 causing the program flow to revert back to step 230. In this manner, the mode cycle signal 170 (FIG. 7) which is stored in the buffer memory 222 is continually accessed and used to create the drive pulses 86 and the patterns of drive pulses which constitute repeating mode cycles of the selected electrosurgical output waveform 52 (FIG. 1).

Referring to FIG. 7, the mode cycle signal 170 is updated periodically by the pattern generation routine 74, as has been described. The memory buffer 222 is preferably a conventional dual port memory, which permits writing signals to memory locations that are not currently being read. In this manner, the updated mode cycle signal 170 replaces the previous mode cycle signal in the buffer memory 222. To the extent that memory locations in the buffer memory 222 are being read at the time that it is desired to update the bytes recorded in those memory locations, the conventional arbitration functionality of the dual port buffer memory 222 will delay writing the bytes of the updated mode cycle signal in those memory locations which are currently being read. After those memory locations have been read by progress of the process flow to a different memory location containing a different byte, as shown by the steps 230, 232 and 234 in FIG. 14, the bytes can then be written into those memory locations.

The DMA controller 220 permits the pattern delivery routine 76 to execute continuously while the electrosurgical generator is activated, thereby continually delivering the drive pulses 86, as shown at 238 in FIG. 8. This continuous execution shown of the pattern delivery routine 76 as shown at 238 in FIG. 8 is facilitated by the pattern generation routine 74 continually updating the mode cycle words 170 (FIG. 7). This permits delivering the drive pulses 86 and the patterns of drive pulses so long as the electrosurgical generator is activated. The DMA controller 220 repeats this process until instructed to stop as a result of the deassertion of the user-initiated activation signal 104 (FIG. 1). Because the pattern delivery routine 76 executes on an autonomous basis as a result of the DMA controller 220 and the automatic updating of the mode cycle signal 170 in the dual port buffer memory 222, the computational resources of the control processor 66 are only occupied to a very minor extent as a result of delivering instructions to the DMA controller 220. The vast majority of the functionality achieved by executing the pattern delivery routine 76 occurs without any impact or influence from the control processor 66.

The power supply control routine 72 sets the magnitude of the output voltage of the high voltage power supply 62 (FIG. 1) in response to the updated pulse width count signal 158, the power set signal 110 and the mode set signal 112. The power supply control routine 72 establishes and delivers a digital power supply control signal 244, shown in FIG. 7. The digital power supply control signal is supplied to a DAC 246 which converts the signal 244 to the power supply voltage control signal 95, also shown in FIG. 1. In response to the power supply voltage control signal 95, the high voltage power supply 62 adjusts its output voltage 94 which is applied to the primary resonant circuit 90 of the RF power amplifier 60, thereby controlling the power delivery from the amplifier 60 along with the effect of the drive pulses 86.

The power supply control routine 72, shown in FIG. 7, includes a high voltage power preset subroutine 250 which is established by the power set signal 110 and the mode set signal 112. The preset subroutine 250 establishes a preset signal 252 based on an anticipated value for the output voltage 94 of the high voltage power supply 62 (FIG. 1). The value of the preset signal 252 is determined by an equation executed by the preset subroutine 250. This equation is based on the selected mode represented by the mode select signal 112, the desired power level represented by the power set signal 110, and other coefficients which are determined experimentally based on the characteristics of the high voltage power supply 62 and the RF power amplifier 60. In general, the value of the preset signal 252 is that value which should result in the desired output power from the output waveform 52 (FIG. 1) along with an anticipated optimal range of power regulation from adjustment of the width of the drive pulses 86 (FIG. 1). The preset signal 252 may be used to initially establish an output voltage from high voltage power supply, so that it may be subsequently modified by execution of the power supply control routine 72. The preset signal 252 may also be used on a continual basis without modification under certain selected modes of operation.

The capability to vary the output voltage 94 from the high voltage power supply 62 (FIG. 1) occurs simultaneously, but considerably more slowly, than the regulation of the output power caused by adjusting the width of the drive pulses 86 (FIG. 1). A preferred pulse width subroutine 254 contributes to this functionality by calculating and supplying a preferred pulse width count signal 256. The preferred pulse width count signal 256 should result in the creation drive pulses 86 (FIG. 1) with widths that will minimize harmonics induced in the primary resonant circuit 90 of the output transformer 92 (FIG. 1), and that will provide the best dynamic range of power control. Minimizing the harmonics has the effect of reducing the amount of leakage current, because the harmonic content represents higher frequencies and higher frequencies generally couple or leak more to the surrounding environment than lower frequencies. Minimizing harmonics is achieved by widening the width of the drive pulses 86. A wider drive pulse contains less high frequency content, and thus less harmonic content. In general, the best dynamic range of power control will be achieved by a pulse width which can increase in size without causing magnetic saturation of the output transformer 92 (FIG. 1) and which is not sufficiently narrow so that it lacks the ability to transfer adequate energy to the resonant circuit 90 (FIG. 1). However, in some circumstances such as open circuit activated conditions, i.e. when the electrosurgical generator is activated but no power is transferred because a current path through the patient has not been established, a greater preferred pulse width count signal 256 may be supplied on a temporary basis to further reduce leakage current.

A comparing function 258 of the power supply control routine 72 compares the updated pulse width count signal 158 to the preferred pulse width count signal 256. The comparing function 258 determines the difference between the preferred pulse width count signal 256 and the updated pulse width count signal 158. Any difference, or error, is supplied to a voltage dynamic compensation subroutine 260. The voltage dynamic compensation subroutine 260 adjusts the amount of error determined by the comparing function 258, in accordance with the amount of current error, the previous value of the power supply control signal 244 and the previous amount of error which existed when the previous power supply control signal 244 was calculated. The execution of the voltage dynamic compensation subroutine 260 results in relatively slow rates of change in the power supply voltage control signal 95, compared to the changes available from adjusting the width of the drive pulses 86. For this reason, the response characteristics from executing the power supply control routine 72 to dynamically adjust the power supply voltage control signal 95 are slower than the response characteristics from executing the pulse width control routine 70. The execution of the voltage dynamic compensation subroutine leads to the delivery of an updated power supply control signal 262.

A select subroutine 264 controls a switch function 266. The switch function 266 selects one of the preset signal 252 or the updated power supply control signal 262 to be supplied as the digital power supply control signal 244. The select subroutine 264 responds to the activation of the electrosurgical generator and, after an appropriate time delay, e.g. 30 milliseconds, delivers a control signal 268 to the switching function 266 to cause the updated power supply voltage control signal 262 to be supplied as the digital power supply control signal 244. In other circumstances when it is desired not to allow the updated pulse width count signal 158 to modify the output voltage 94 of the high voltage power supply 62 (FIG. 1), the select subroutine 264 controls the switching function 266 to continually supply the preset signal 252 as the digital power supply control signal 244. In a typical circumstance, the select subroutine initially supplies the preset signal 252 to control the output voltage from the high voltage power supply 62 (FIG. 1). However within a short time after operation commences, the updated power supply voltage control signal 262 is supplied to permit a dynamic response in regulating the output voltage of the high voltage power supply relative to the pulse width of the drive pulse 86. In this manner, the dynamic regulation capability from the drive pulses 86 is optimized and the leakage current is minimized by reducing harmonics induced in the output waveform 52.

Figure 15:
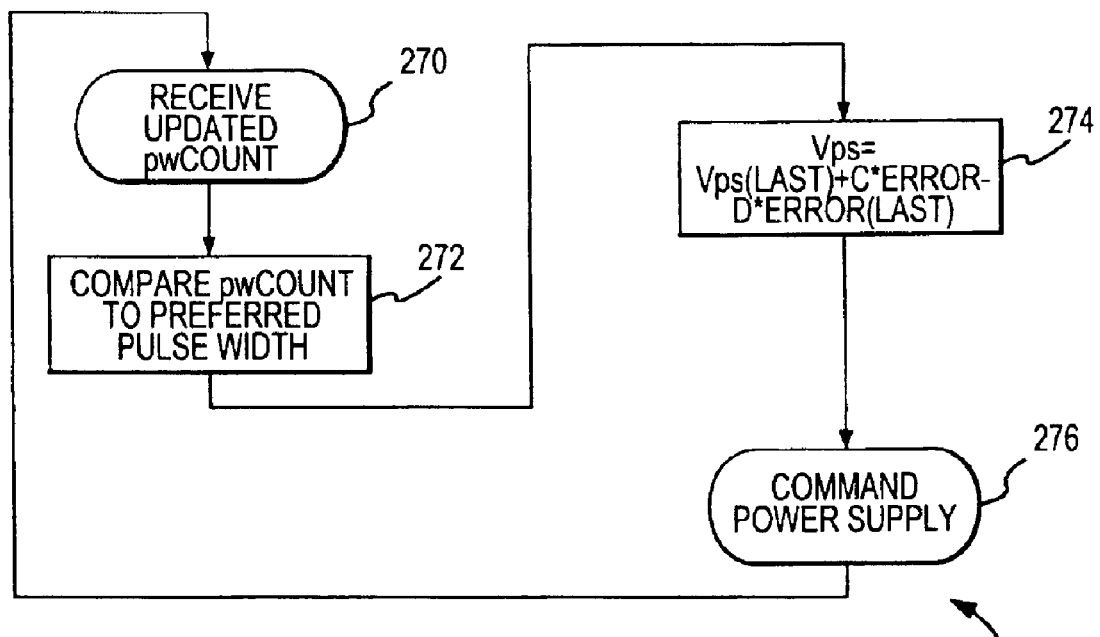
FIG. 15 is a flowchart illustrating functions performed when executing a power supply control routine shown in FIG. 6.

The process flow for executing dynamic voltage control aspects of the power supply control routine 72 is shown in FIG. 15, including the steps involved in executing the voltage dynamic compensation subroutine 260. At step 270, the updated pulse width count signal (pwCount, 158 shown in FIG. 7) is received. At step 272, the updated pulse width count signal is compared to the preferred pulse width signal 256 (FIG. 7). The error derived from the comparison at step 272 is used at step 274 in the voltage dynamic compensation subroutine at 260 (FIG. 7). The voltage dynamic compensation subroutine is executed as shown at step 274 by starting with the previous value (Vps(last)) of the power supply voltage control signal (262, FIG. 7) that was calculated at the previous execution of the power supply control routine 76. Added to that previous value of the power supply voltage control signal is the currently determined error multiplied by a compensation factor (C). From this resulting value there is subtracted the value of the previous error obtained by executing the power supply control routine 76 previously multiplied by another compensation factor (D). The result constitutes the updated voltage power supply control signal 262. The voltage dynamic compensation subroutine 260 uses a similar functional basis as the pulse width dynamic compensation subroutine 156 previously described in conjunction with FIG. 12, and the compensation factors (C) and (D) are selected and determined to obtain the desired responsiveness under conventional control system analysis.

The updated voltage power supply control signal created from the voltage dynamic compensation subroutine (260, FIG. 7) at step 274 is then delivered at step 276 to constitute the digital power supply control signal 244 (FIG. 7). As shown in FIG. 7, the signal 244 is converted by the DAC 246 to create the power supply voltage control signal 95 used to vary the output voltage 94 of the high voltage power supply 62 (FIG. 1).

The ability of the pulse generation routine 74 to discharge or damp energy from the resonant circuit 90 of the output transformer 92 is also particularly useful for modifying the output characteristics of the output waveform 52, as understood from FIG. 1. Damping the energy from the resonant circuit 90 offers a complementary and different way of controlling the RF power amplifier 60 which cannot be achieved by adjusting the width and pattern of the drive pulses 86. For example, once a drive pulse 86 is delivered to the resonant circuit 90, the response of the RF power amplifier 60 can no longer be controlled by the adjusting the width and pattern of the drive pulses. The damping capability offers the ability to modify the response of the RF power amplifier, after the drive pulses 86 have been delivered.

An example of the energy damping capability available from the pattern generation routine 74 is illustrated in FIGS. 16–18. The exemplary situation shown in FIGS. 16–18 involves the delivery of a single relatively long drive pulse 86a during a spray coagulation mode of operation of the electrosurgical generator. Only the one relatively long drive pulse 86a is delivered during each mode cycle of spray coagulation, as is conventional. Consequently, the relatively wide width of the drive pulse 86a will result in considerable energy being delivered into the resonant circuit 90 (FIG. 1). The relatively high energy content of the resonant circuit will create a relatively high voltage output waveform 52a, as shown in FIG. 17. Because of the relatively high Q of the resonant circuit 90 (FIG. 1) used for spray coagulation, the oscillation of the energy in the resonant circuit may continue for some relatively significant time, with the resulting output waveform 52a also continuing for a relatively long time duration compared to the width of the drive pulse 86a, as shown in FIGS. 16 and 17. In general, the greatest effect from spray coagulation results in the early part of the output waveform 52a, after approximately two to four oscillations of the output waveform 52a have been delivered. Any further surgical effect on the tissue is minimal or nonexistent after these initial two to four oscillations. However, because energy still exists in the resonant circuit (90, FIG. 1) after the initial two to four oscillations, the oscillations will continue to transfer energy into the tissue until the energy naturally decays. Transferring energy into the tissue may create a detrimental effect with no corresponding surgical benefit, so it is desirable to avoid transferring any more energy to the tissue than is necessary to achieve the desired surgical effect. Excess energy transfer negatively impacts the tissue, such as by unnecessarily heating it. The existence of excess energy also contributes to leakage current.

The assertion of the damping signal 96 (FIG. 1) by the pattern generation routine 74 eliminates or significantly reduces the excess energy in the resonant circuit, as shown in FIGS. 17–18. A damping signal waveform 280, shown in FIG. 18, is created by asserting the damping signal 96 to cause the damping transistor 97 (FIG. 1) to cease conducting at time 282. The non-conductive damping transistor 97 (FIG. 1) allows all of the energy of the spray coagulation drive pulse 86a (FIG. 16) to achieve its maximum oscillatory effect for a few cycles, until a time 284 when the damping signal 96 (FIG. 1) is again asserted, causing the damping transistor 97 to conduct energy from the resonant circuit 90 (FIG. 1). Commencing at time 284, the output waveform quickly dissipates, as shown by the modified ending portion 52b of the waveform which occurs after time 284. The rapid decay of the output waveform portion 52b results because the conductive damping transistor 97 removes energy from the resonant circuit 90. Consequently, the excess energy in the waveform 52a existing after the time 284 is not transferred to the tissue of the patient and is not allowed to generate leakage current, but instead is damped or removed from the resonant circuit 90 (FIG. 1). However, the effective surgical effect from spray coagulation is achieved by allowing the first few oscillations of the output waveform 52a to achieve a relatively high voltage before the damping occurs at time 284.

In this particular example, a relatively high "crest factor" is obtained. "Crest factor" is a well known electrosurgical term used to describe a ratio of the peak voltage to the RMS voltage over a given time. A high crest factor is desirable in spray coagulation. A high crest factor is apparent in FIG. 17, because of the relatively high voltage during the first few oscillations of the waveform, followed by a much longer period of relatively low or insignificant voltage of the waveform portion 52b as a result of the damping achieved after time 284. The much longer period of relatively lower voltage significantly reduces the RMS voltage over the spray coagulation mode cycle.

There are a number of other reasons for damping energy from the resonant circuit 90 of the RF power amplifier 60. Some of those reasons include minimizing leakage current under certain operating conditions, creating or sustaining ionization effects in the air or gas surrounding the active electrode which applies the output waveform to the tissue, and creating specialized surgical effects useful in specialized surgical procedures. In general, offering the possibility of damping or modifying the energy content after delivery to the resonant circuit is another approach to controlling the electrosurgical output and performance characteristics which may not obtained from controlling the characteristics of the drive pulses 86 supplied to the RF power amplifier 60. Moreover, the damping effect can be used in combination with the power delivery effect created by regulating the width and pattern of the drive pulses 86, to achieve a desired and beneficial electrosurgical effect not achievable by either control technique by itself.

The previous description describes many examples of the many improvements available from the present invention. The flexibility to adapt an existing electrosurgical generator to new and different operational modes and functional features is obtained by modifying the software and instructional code involved in executing the various routines. The flexibility to modify these routines is available to accommodate and to add new modes of operation to an electrosurgical generator and to optimize its performance for specialized surgical procedures, as well as to improve the effect achieved from existing modes of operation. The flexibility to adapt the operating conditions of the electrosurgical generator for safety purposes and for improved power regulation is also available from the software and instructional code involved in these operational and control system routines. Many other advantages and improvements will be apparent upon gaining a complete understanding and appreciation of the nature of the present invention.

Presently preferred embodiments of the invention and many of its improvements have been described with a degree of particularity. This description is a preferred example of implementing the invention, and is not intended to limit the scope of the invention which is defined by the following claims.

What is claimed is:

1. An electrosurgical generator which creates and delivers a radio frequency electrosurgical output waveform, the electrosurgical generator having a controller which executes instructional code of a plurality of interactive routines to cooperatively create drive pulses in response to a selected one of a plurality of selectable modes of operation and a selected one of a plurality of selectable output power levels within the selected mode of operation and an actual power output level of the output waveform, the controller applying the drive pulses to an output circuit which converts energy represented by the drive pulses into the output waveform, the drive pulses applied to the output circuit establishing mode characteristics and the actual power output level of the output waveform, the output waveform having an analog output voltage and an analog output current, and wherein the routines and operations executed by the controller comprise:

a sampling routine which obtains a plurality of time-spaced sample values corresponding to the analog output voltage and the analog output current of the output waveform at the time when each sample value is obtained, the sampling routine obtaining the plurality of sample values during each of a plurality of sequential sampling intervals;

a pulse control routine which establishes a pulse-defining value for the drive pulses during each sampling interval, the pulse control routine establishing the pulse-defining value during each sampling interval by use of the selected output power level and the sample values obtained over a preceding sampling interval which preceded a present sampling interval in which the sampling routine presently obtains the sample values;

a pattern generation routine which generates a mode cycle pattern for a plurality of drive pulses, the pattern generation routine generating the mode cycle pattern during the present sampling interval in accordance with the selected mode of operation and the pulse-defining value established by the pulse control routine during the present sampling interval; and a pattern delivery routine which creates the drive pulses by sequentially delivering to the output circuit multiple ones of the generated mode cycle pattern with the drive pulses of the delivered mode cycle patterns having the established pulse-defining value.

2. An electrosurgical generator as defined in claim 1, wherein:

the pulse-defining value established by the pulse control routine is a width value for the drive pulses.

3. An electrosurgical generator which creates and delivers a radio frequency electrosurgical output waveform, the electrosurgical generator having a controller which executes instructional code of a plurality of interactive routines to cooperatively create drive pulses in response to a selected one of a plurality of selectable modes of operation and a selected one of a plurality of selectable output power levels within the selected mode of operation and an actual power output level of the output waveform, the controller applying the drive pulses to an output circuit which converts energy represented by the drive pulses into the output waveform, the drive pulses applied to the output circuit establishing mode characteristics and the actual power output level of the output waveform, the output waveform having an analog output voltage and an analog output current, and wherein the routines and operations executed by the controller comprise:

a sampling routine which obtains a plurality of time-spaced sample values corresponding to the analog output voltage and the analog output current at the time when each sample value is obtained, the sampling routine obtaining the plurality of sample values during a sampling interval;

a pulse control routine which establishes a pulse-defining value for the drive pulses by using the sample values and the selected output power level, the pulse-defining value constituting a width value for the drive pulses;

a power supply control routine which establishes a voltage level for transferring energy to the output circuit in response to the applied drive pulses;

a pattern generation routine which generates a mode cycle pattern for a plurality of the drive pulses in accordance with the selected mode of operation; and a pattern delivery routine which creates the drive pulses by sequentially delivering to the output circuit multiple ones of the generated mode cycle pattern with the drive pulses of the delivered mode cycle patterns having the width value established by the pulse control routine; and wherein:

the pulse control routine dynamically adjusts the width value for the drive pulses during the delivery of the output waveform;

the power supply control routine dynamically adjusts the voltage level during the delivery of the output waveform; and the power supply control routine dynamically adjusts the voltage level at a slower rate than the pulse control routine dynamically adjusts the width value for the drive pulses.

4. An electrosurgical generator which regulates output power of a delivered electrosurgical output waveform, the output waveform having a primary radio frequency and being defined by an analog output voltage and an analog output current, the electrosurgical generator comprising:

a controller which obtains a plurality of time-spaced sample values which correspond to one or both of an instantaneous value of the analog output voltage and an instantaneous value of the analog output current at the time when each sample value is obtained; and wherein:

the controller obtains the sample values at a sampling rate which is less than a Nyquist rate for the primary radio frequency;

the controller performs a calculation using the sample values to derive a power-related quantity related to the actual output power level of the delivered output waveform; and the controller regulates the actual output cower level of the delivered output waveform in relation to the power-related quantity.

5. An electrosurgical generator as defined in claim 4, further comprising:

a power selector to establish a selected output power level at which to deliver the output waveform; and wherein:

the plurality of sample values obtained correspond to both the analog output voltage and the analog output current;

the controller performs the calculation using the sample values corresponding to both the analog output voltage and the analog output current to derive the power-related quantity;

the controller regulates the actual output power level of the delivered output waveform based on a comparison of the power-related quantity and the selected output power level.

6. An electrosurgical generator as defined in claim 5, wherein:

the plurality of sample values obtained constitute a block of sample values obtained during a sampling interval, the sampling interval extends over a plurality of cycles of the radio frequency output waveform, the block of sample values including sample values corresponding to both the analog output voltage and the analog output current occurring during the sampling interval in which the block of sample values was obtained; and the controller calculates an average power value as the power-related quantity by performing a calculation which includes a root mean square calculation using the block of sample values of output voltage and output current obtained during the sampling interval.

7. An electrosurgical generator as defined in claim 6, further comprising:

an output circuit which creates the output waveform in response to the application of drive pulses, each drive pulse representing energy transferred to the output circuit for use in creating the output waveform; and wherein:

the controller creates the drive pulses and applies the drive pulses to the output circuit to create the output waveform.

8. An electrosurgical generator as defined in claim 7, further comprising:

a mode selector to establish a selected mode of operation; and wherein:

the controller executes instructional code of a plurality of routines which cooperatively create the drive pulses in response to the selected output power level and the selected mode of operation and the output power of the output waveform, the routines and operations executed by the controller comprise:

a sampling routine which obtains the plurality of sample values during the sampling interval;

a pulse control routine which establishes a pulse-defining value for the drive pulses by using the average power value and a comparison of the average power value and the selected output power level, the pulse-defining value constituting a width value for the drive pulses;

a pattern generation routine which generates a mode cycle pattern for a plurality of the drive pulses in accordance with the selected mode of operation; and a pattern delivery routine which creates the drive pulses by sequentially delivering to the output circuit multiple ones of the generated mode cycle pattern with the drive pulses of the delivered mode cycle patterns having the established pulse-defining value.

9. An electrosurgical generator which creates and delivers a radio frequency electrosurgical output waveform, the electrosurgical generator having a controller which executes instructional code of a plurality of interactive routines to cooperatively create drive pulses in response to a selected one of a plurality of selectable modes of operation and a selected one of a plurality of selectable output power levels within the selected mode of operation and an actual power output level of the output waveform, the controller applying the drive pulses to an output circuit which converts energy represented by the drive pulses into the output waveform, the drive pulses applied to the output circuit establishing mode characteristics and the actual cower output level of the output waveform, the output waveform having an analog output voltage and an analog output current, and wherein the routines and operations executed by the controller comprise:

a sampling routine which obtains a plurality of time-spaced sample values corresponding to the analog output voltage and the analog output current at the time when each sample value is obtained, the sampling routine obtaining the plurality of sample values during each of a series of sampling intervals, the plurality of sample values obtained during each sampling interval constituting a block of sample values, the sampling routine obtaining a series of blocks of sample values during a corresponding series of the sampling intervals;

a pulse control routine which establishes a pulse-defining value for the drive pulses by using one block of sample values and the selected output power level, the pulse control routine establishing the pulse-defining value by use of a preceding block of sample values obtained during a preceding sampling interval which preceded a present sampling interval in which the sampling routine presently obtains a present block of sample values, the pulse control routine establishing the pulse-defining value simultaneously with the sampling routine obtaining the present block of sample values;

a pattern generation routine which generates a mode cycle pattern for a plurality of the drive pulses in accordance with the selected mode of operation; and a pattern delivery routine which creates the drive pulses by sequentially delivering to the output circuit multiple ones of the generated mode cycle pattern with the drive pulses of the delivered mode cycle patterns having the established pulse-defining value.

10. An electrosurgical generator as defined in claim 9, wherein:

the pulse-defining value established by the pulse control routine is a width value for the drive pulses.

11. An electrosurgical generator which creates and delivers a radio frequency electrosurgical output waveform, the electrosurgical generator having a controller which executes instructional code of a plurality of interactive routines to cooperatively create drive pulses in response to a selected one of a plurality of selectable modes of operation and a selected one of a plurality of selectable output power levels within the selected mode of operation and an actual power output level of the output waveform, the controller applying the drive pulses to an output circuit which converts energy represented by the drive pulses into the output waveform, the drive pulses applied to the output circuit establishing mode characteristics and the actual power output level of the output waveform, the output waveform having an analog output voltage and an analog output current, and wherein the routines and operations executed by the controller comprise:

a sampling routine which obtains a plurality of time-spaced sample values corresponding to the analog output voltage and the analog output current at the time when each sample value is obtained, the sampling routine obtaining the plurality of sample values during a sampling interval;

a pulse control routine which establishes a pulse-defining value for the drive pulses by using the sample values and the selected output power level, the pulse-defining value constituting a width value for the drive pulses;

a pattern generation routine which generates a mode cycle pattern for a plurality of the drive pulses in accordance with the selected mode of operation and the pulse width established by the pulse control routine;

a pattern delivery routine which creates the drive pulses by sequentially delivering to the output circuit multiple ones of the generated mode cycle pattern; and wherein:

the pattern generation routine changes the width value for at least one but not all of the drive pulses within the generated mode cycle pattern after the width value of those pulses has been initially established by the pulse control routine.

12. An electrosurgical generator as defined in claim 11, wherein:

the pattern generation routine changes the width value for at least one but not all of the drive pulses within the generated mode cycle pattern to adjust average power over the generated mode cycle pattern to a level that cannot be achieved by establishing the same width value for all of the drive pulses within the generated mode cycle pattern.

13. An electrosurgical generator which creates and delivers a radio frequency electrosurgical output waveform, the electrosurgical generator having a controller which executes instructional code of a plurality of interactive routines to cooperatively create drive pulses in response to a selected one of a plurality of selectable modes of operation and a selected one of a plurality of selectable output power levels within the selected mode of operation and an actual power output level of the output waveform, the controller applying the drive pulses to an output circuit which converts energy represented by the drive pulses into the output waveform, the drive pulses applied to the output circuit establishing mode characteristics and the actual power output level of the output waveform, the output waveform having an analog output voltage and an analog output current, and wherein the routines and operations executed by the controller comprise:

a sampling routine which obtains a plurality of time-spaced sample values corresponding to the analog output voltage and the analog output current at the time when each sample value is obtained, the sampling routine obtaining the plurality of sample values during a sampling interval;

a pulse control routine which establishes a pulse-defining value for the drive pulses by using the sample values and the selected output power level;

a pattern generation routine which generates a mode cycle pattern for a plurality of the drive pulses in accordance with the selected mode of operation; and a pattern delivery routine which creates the drive pulses by sequentially delivering to the output circuit multiple ones of the generated mode cycle pattern with the drive pulses of the delivered mode cycle patterns having the established pulse-defining value; and wherein:

the controller selectively dissipates energy previously transferred to the output circuit by the drive pulses after delivery of the output waveform has commenced.

14. An electrosurgical generator as defined in claim 13, wherein:

the controller selectively dissipates energy from the output circuit after delivery of the output waveform has commenced from the energy represented by the drive pulses of one delivered generated mode cycle pattern.

15. An electrosurgical generator as defined in claim 13, wherein:

the pulse-defining value established by the pulse control routine is a width value for the drive pulses.

16. An electrosurgical generator as defined in claims 2, 11, 8, 10 or 15, further comprising:

a power supply control routine which establishes a voltage level for transferring energy to the output circuit in response to the applied drive pulses, the power supply control routine establishing the voltage level in a coordinated relationship with the width value established by the pulse control routine.

17. An electrosurgical generator as defined in claim 16, wherein:

the pulse control routine dynamically adjusts the width value for the drive pulses during the delivery of the output waveform;

the power supply control routine dynamically adjusts the voltage level during the delivery of the output waveform; and the power supply control routine dynamically adjusts the voltage level at a slower rate than the pulse control routine dynamically adjusts the width value for the drive pulses.

18. An electrosurgical generator as defined in claims 3, 8, 10 or 15, wherein:

the pattern generation routine changes the width value for at least one but not all of the drive pulses within the generated mode cycle pattern after the width value for those pulses has been initially established by the pulse control routine.

19. An electrosurgical generator as defined in claim 18, wherein:

the pattern generator routine changes the width value for at least one but not all of the drive pulses within the generated mode cycle pattern to adjust average power over the generated mode cycle pattern to a level that cannot be achieved by establishing the same width value for all of the drive pulses within the generated mode cycle pattern.

20. An electrosurgical generator as defined in claims 3, 11, 13 or 8, wherein:

the sampling routine obtains the sample values while the pulse control routine establishes the pulse-defining value and while the pattern generation routine generates the mode cycle pattern.

21. An electrosurgical generator as defined in claims 3, 9, 11, 13 or 8, wherein:

the pattern delivery routine continually delivers the generated mode cycle patterns while the sampling routine obtains the sample values.

22. An electrosurgical generator as defined in claims 3, 11, 13 or 8, wherein:

the plurality of sample values obtained during the sampling interval constituting a block of sample values, the sampling routine obtaining a series of blocks of sample values during a corresponding series of the sampling intervals;

the pulse control routine establishes the pulse-defining value during each sampling interval by using one block of sample values;

the pattern generation routine generates the mode cycle pattern during a present sampling interval using the pulse-defining value established by the pulse control routine during the present sampling interval; and the pulse control routine establishes the pulse-defining value during the present sampling interval by use of a preceding block of sample values obtained during a preceding sampling interval which preceded the present sampling interval in which the sampling routine presently obtains the present block of sample values.

23. An electrosurgical generator as defined in claims 3, 9, 11, 13 or 8, further including direct memory access components with which the controller interacts, and wherein:

the sampling routine records the plurality of sample values in the direct memory access components without requiring the execution of instructional code after recording of the sample values has commenced during each sampling interval; and the pattern delivery routine utilizes the direct memory access components to sequentially deliver the multiple ones of the generated mode cycle pattern without requiring the execution of instructional code after commencing delivery of the generated mode cycle patterns.

24. An electrosurgical generator as defined in claims 3, 9, 13 or 8, wherein:

the pattern generation routine includes the pulse-defining value established by the pulse control routine within the generated mode cycle pattern.

25. An electrosurgical generator as defined in claims 3, 9, 11, 13 or 6, wherein:

the sampling routine obtains the sample values of the output voltage and the output current on an alternating basis.

26. An electrosurgical generator as defined in claims 3, 9, 11, 13 or 8, further including an analog to digital converter receptive of the sample values and operative to convert the instantaneous sample values of the analog output voltage and the analog output current into corresponding digital sample values, and a memory having a plurality of memory locations, and wherein:

the sampling routine fills a first plurality of memory locations of the memory with the plurality of digital sample values obtained from one sampling interval and fills a second plurality of memory locations of the memory with the plurality of digital sample values obtained from the next subsequent sampling interval; and the sampling routine performs a mathematical calculation using the sample values from one of the first and second pluralities of memory locations to derive an average power value representative of the actual output power level of the delivered output waveform during the corresponding one sample interval, and then alternately performs the same mathematical calculation using the sample values from the other one of the first and second pluralities of memory locations to derive an average power value representative of the actual output power of the delivered output waveform during the other one of the sample intervals.

27. An electrosurgical generator as defined in claim 26, wherein:

the sampling routine obtains a plurality of sample values of output voltage and a plurality of samples of output current during each sample interval;

the sampling routine obtains one sample value at a time;

the sampling routine obtains the sample values of the output voltage and the output current on an alternating basis; and the sampling routine sequentially fills the memory locations of each of the first and second pluralities of memory locations with the sample values in the order in which the sample values are obtained.

28. An electrosurgical generator as defined in claims 3, 9, 11, 13 or 8, wherein:

the sampling routine obtains a plurality of sample values of the output voltage and a plurality of sample values of the output current during each sampling interval;

the pulse control routine calculates an error value during each sampling interval by subtracting from the selected output power level a power value obtained from a calculation using the plurality of sample values obtained during one sampling interval;

the pulse control routine retains a preceding pulse-defining value and a preceding error value applicable to a preceding sampling interval which preceded a present sampling interval in which the sampling routine is presently obtaining the sample values;

the pulse control routine calculates a present error value obtained from the calculation of the error value during a present sampling interval; and the pulse control routine establishes a present pulse-defining value during the present sampling interval by performing a calculation which includes multiplying the present error value and the preceding pulse-defining value and a first compensating factor and thereafter subtracting the product of the preceding error value and the preceding pulse-defining value and a second compensating factor.

29. An electrosurgical generator as defined in claims 3, 9, 11, 13 or 8, wherein:

the pulse control routine establishes the pulse-defining value during each sampling interval by performing a calculation using the plurality of sample values obtained; and further comprising:

a power supply control routine which establishes a voltage level for transferring energy to the output circuit in response to the applied drive pulses, the power supply control routine establishing the voltage level in a coordinated relationship with a preferred pulse-defining value, the power supply routine establishing the preferred pulse-defining value in relation to a present pulse-defining value established by the pulse control routine during a present sampling interval;

the power supply control routine calculating a present voltage error value during the present sampling interval by comparing the present pulse-defining value with the preferred pulse-defining value during the present sampling interval; and the power supply control routine adjusting the voltage level relative to an existing voltage level by adding to the existing voltage level an amount obtained by performing a calculation which includes multiplying the present voltage error value and a first compensating factor and by thereafter subtracting the product of a second compensating factor and a preceding voltage error value obtained by the same calculation performed during a preceding sampling interval.

30. An electrosurgical generator as defined in claims 3, 9, 11, or 7, wherein:

the controller selectively dissipates energy previously transferred to the output circuit by the drive pulses after delivery of the output waveform has commenced.

31. An electrosurgical generator as defined in claim 30, wherein:

the controller selectively dissipates the energy previously transferred to the output circuit by the drive pulses from one delivered generated mode cycle pattern after delivery of the output waveform has commenced.

32. An electrosurgical generator as defined in claims 3, 9, 11 or 13, wherein:

the sampling routine obtains the sample values at a sampling rate which is less than a Nyquist rate for the primary radio frequency of the output waveform.

33. An electrosurgical generator as defined in claim 32, wherein:

the sampling routine obtains sample values corresponding to both the analog output voltage and the analog output current;

the pulse control routine performs a calculation which includes a root mean square calculation using the sample values corresponding to both the analog output voltage and the analog output current to derive an average power value related to the actual power output level; and the pulse control routine establishes the pulse-defining value in relation to the average power value.

34. An electrosurgical generator as defined in claim 33, further comprising:

the pulse control routine establishes the pulse-defining value by using a comparison of the average power value and the selected output power level.

35. An electrosurgical generator as defined in claims 3, 9, 11 or 13, wherein:

the pulse control routine establishes the pulse-defining value by performing a calculation using the sample values to derive a power-related quantity.

36. An electrosurgical generator as defined in claim 35, wherein:

the pulse control routine calculates an average power value as the power-related quantity by performing a calculation which includes a root mean square calculation using sample values corresponding to both the analog output voltage and the analog output current.

37. A method of creating and delivering a radio frequency electrosurgical output waveform defined by an analog output voltage and an analog output current comprising: selecting a modes of operation to characterize the output waveform;

selecting an output power level for the output waveform for the selected mode of operation;

converting energy represented by drive pulses into the output waveform;

establishing mode characteristics and an actual power output level of the output waveform from the drive pulses;

obtaining a plurality of time-spaced sample values corresponding to the analog output voltage and the analog output current at the time when each sample value is obtained;

obtaining the plurality of sample values during each of a plurality of sequentially occurring sampling intervals;

establishing a pulse-defining value for the drive pulses during each sampling interval by use of the selected output power level and the sample values obtained over a preceding sampling interval which preceded a present sampling interval in which sample values are presently being obtained;

generating a mode cycle pattern for a plurality of drive pulses during the present sampling interval in accordance with the selected mode of operation and the pulse-defining value established during the present sampling interval; and creating the drive pulses by sequentially delivering multiple ones of the generated mode cycle pattern with the drive pulses of the delivered mode cycle patterns having the established pulse-defining value.

38. A method as defined in claim 37, further comprising:

establishing the pulse-defining value as a width value for the drive pulses.

39. A method of creating and delivering a radio frequency electrosurgical output waveform defined by an analog output voltage and an analog output current, comprising:

selecting a mode of operation to characterize the output waveform;

selecting an output power level for the output waveform for the selected mode of operation;

converting energy represented by drive pulses into the output waveform;

establishing mode characteristics and an actual power output level of the output waveform from the drive pulses;

obtaining a plurality of time-spaced sample values corresponding to the analog output voltage and the analog output current at the time when each sample value is obtained;

obtaining the plurality of sample values during a sampling interval;

establishing a pulse-defining value for the drive pulses by using the selected output power level and a calculation using the sample values to derive a power-related quantity, the pulse-defining value constituting a width value for the drive pulses;

establishing a voltage level for converting the energy represented by the drive pulses into the output waveform;

generating a mode cycle pattern for a plurality of the drive pulses in accordance with the selected mode of operation;

creating the drive pulses by sequentially delivering multiple ones of the generated mode cycle pattern with the drive pulses of the delivered mode cycle patterns having the established width value;

dynamically adjusting the width value for the drive pulses during the delivery of the output waveform;

dynamically adjusting the voltage level for converting the energy represented by the drive pulses during the delivery of the output waveform; and dynamically adjusting the voltage level at a slower rate of than the width value is dynamically adjusted.

40. A method as defined in claims 12, 14, 26 or 25, further comprising:

including the established pulse-defining value within the generated mode cycle pattern.

41. A method of creating and delivering a radio frequency electrosurgical output waveform defined by an analog output voltage and an analog output current, comprising:

selecting a mode of operation to characterize the output waveform;

selecting an output power level for the output waveform for the selected mode of operation;

converting energy represented by drive pulses into the output waveform;

establishing mode characteristics and an actual power output level of the output waveform from the drive pulses;

obtaining a plurality of time-spaced sample values corresponding to the analog output voltage and the analog output current at the time when each sample value is obtained;

obtaining a plurality of sample values during each of a series of sampling intervals;

constituting a block of sample values from the plurality of sample values obtained during each sampling interval;

obtaining a series of blocks of sample values during a corresponding series of sampling intervals;

establishing a pulse-defining value for the drive pulses by using a block of sample values and the selected output power level;

establishing the pulse-defining value during a present sampling interval simultaneously with obtaining a present block of sample values;

using a preceding block of sample values which was obtained in a preceding sampling interval which preceded the present sampling interval to establish the pulse-defining value for the drive pulses during the present sampling interval;

generating a mode cycle pattern for a plurality of the drive pulses in accordance with the selected mode of operation; and creating the drive pulses by sequentially delivering multiple ones of the generated mode cycle pattern with the drive pulses of the delivered mode cycle patterns having the established pulse-defining value.

42. A method as defined in claim 41, further comprising:

establishing the pulse-defining value as a width value for the drive pulses.

43. A method of creating and delivering a radio frequency electrosurgical output waveform defined by an analog output voltage and an analog output current, comprising:

selecting a mode of operation to characterize the output waveform;

selecting an output power level for the output waveform for the selected mode of operation;

converting energy represented by drive pulses into the output waveform;

establishing mode characteristics and an actual power output level of the output waveform from the drive pulses;

obtaining a plurality of time-spaced sample values corresponding to the analog output voltage and the analog output current at the time when each sample value is obtained;

obtaining the plurality of sample values during a sampling interval;

establishing a pulse-defining value for the drive pulses by using the sample values and the selected output power level, the pulse-defining value constituting a width value for the drive pulses;

generating a mode cycle pattern for a plurality of the drive pulses in accordance with the selected mode of operation and the established width value;

creating the drive pulses by sequentially delivering multiple ones of the generated mode cycle pattern; and changing the width value for at least one but not all of a plurality of drive pulses within the generated mode cycle pattern after the width value for those drive pulses has been initially established but before creating the drive pulses using the delivered mode cycle patterns.

44. A method as defined in claim 43, further comprising:

changing the width value for at least one but not all of the drive pulses to adjust average power over the generated mode cycle pattern to a level that cannot be achieved by establishing the same width value for all of the drive pulses within the generated mode cycle pattern.

45. A method as defined in claim 43, further comprising:

changing the width value for at least one but not all of the drive pulses within the generated mode cycle pattern to adjust average power over the generated mode cycle pattern to a level that cannot be achieved by establishing the same width value for all of the drive pulses within the generated mode cycle pattern.

46. A method of regulating output power of a delivered electrosurgical output waveform, the output waveform having a primary radio frequency and being defined by an analog output voltage and an analog output current, comprising:

obtaining a plurality of time-spaced sample values which correspond to one or both of an instantaneous value of the output voltage and an instantaneous value of the output current at the time when each sample is obtained;

obtaining the sample values at a sampling rate which is less than a Nyquist rate for the primary radio frequency;

performing a calculation using the sample values to derive a power-related quantity related to an actual output power level of the delivered output waveform; and regulating the actual output power level of the delivered output waveform in relation to the power-related quantity.

47. A method as defined in claim 46, further comprising:

selecting an output power level at which to deliver the output waveform;

obtaining the plurality of sample values which correspond to both the analog output voltage and the analog output current;

performing the calculation using the sample values which correspond to both the analog output voltage and the analog output current to derive the power-related quantity; and regulating the actual output power level of the delivered output waveform based on a comparison of the power-related quantity and the selected output power level.

48. A method as defined in claim 47, further comprising:

obtaining a block of sample values during a sampling interval;

extending the sampling interval during which each block is obtained over a plurality of cycles of the radio frequency output waveform;

constituting each block with sample values corresponding to both the analog output voltage and the analog output current occurring during the sampling interval in which the block of sample values was obtained; and calculating an average power value as the power-related quantity by performing a calculation which includes a root mean square calculation using the block of sample values of output voltage and output current obtained during the sampling interval.

49. A method as defined in claim 48, further comprising:

creating the output waveform from energy represented by drive pulses; and transferring the energy represented the drive pulses into the output waveform.

50. A method as defined in claim 49, further comprising:

selecting a mode of operation;

establishing a pulse-defining value for the drive pulses by using the average power value and a comparison of the average power value and the selected output power level, the pulse-defining value constituting a width value for the drive pulses;

generating a mode cycle pattern for a plurality of the drive pulses in accordance with the selected mode of operation; and sequentially delivering multiple ones of the generated mode cycle pattern with the drive pulses of the delivered mode cycle patterns having the established pulse-defining value.

51. A method of creating and delivering a radio frequency electrosurgical output waveform defined by an analog output voltage and an analog output current, comprising:

selecting a mode of operation to characterize the output waveform;

selecting an output power level for the output waveform for the selected mode of operation;

converting energy represented by drive pulses into the output waveform;

establishing mode characteristics and an actual power output level of the output waveform from the drive pulses;

obtaining a plurality of time-spaced sample values corresponding to the analog output voltage and the analog output current of the output waveform at the time when each sample value is obtained;

obtaining the plurality of sample values during a sampling interval;

establishing a pulse-defining value for the drive pulses by using the sample values and the selected output power level;

generating a mode cycle pattern for a plurality of the drive pulses in accordance with the selected mode of operation;

creating the drive pulses by sequentially delivering multiple ones of the generated mode cycle pattern with the drive pulses of the delivered mode cycle patterns having the established pulse-defining value; and transferring the energy to be converted into the output waveform to an output circuit;

delivering the output waveform from the output circuit; and selectively dissipating some of the previously transferred energy from the output circuit of before that energy is converted into the output waveform.

52. A method as defined in claim 51, further comprising:

establishing the pulse-defining value as a width value for the drive pulses.

53. A method as defined in claim 51, comprising:

selectively dissipating some of the energy previously transferred to the output circuit after delivery of the output waveform has commenced from the energy represented by the drive pulses of one delivered generated mode cycle pattern.

54. A method as defined in claims 38, 43, 50, 42 or 52, further comprising:

establishing a voltage level for converting energy represented by the drive pulses into the output waveform in respect to the drive pulses.

55. A method as defined in claim 54, further comprising:

coordinating the established voltage level to the width value established for the drive pulses.

56. A method as defined in claim 55, further comprising:

dynamically adjusting the width value for the drive pulses during delivery of the output waveform;

dynamically adjusting the voltage level during delivery of the output waveform; and dynamically adjusting the voltage level at a slower rate than the width value for the drive pulses is dynamically adjusted.

57. A method as defined in claims 38, 39, 50, 42 or 52, further comprising:

changing the width value for at least one but not all of the drive pulses within the generated mode cycle pattern after the width value for those pulses has been initially established.

58. A method as defined in claims 39, 43, 51 or 50, further comprising:

obtaining sample values while establishing the pulse-defining value for the drive pulses and while generating the mode cycle pattern.

59. A method as defined in claims 37, 39, 41, 43, 51 or 50, further comprising:

continually delivering the mode cycle pattern while obtaining the sample valves.

60. A method as defined in claims 39, 43, 51 or 50, further comprising:

constituting a block of sample values from the plurality of sample values obtained during the sampling interval;

obtaining a series of blocks of sample values during a corresponding series of sampling intervals;

establishing the pulse-defining value during each sampling interval by using one block of sample values;

establishing the pulse-defining value during a present sampling interval by use of a preceding block of sample values obtained during a preceding sampling interval which preceded the present sampling interval in which a present block of sample values is obtained; and generating the mode cycle pattern during the present sampling interval by using the pulse-defining value established by using the preceding block of sample values.

61. A method as defined in claims 37, 39, 41, 43, 51 or 49, further comprising:

transferring the energy to be converted into the output waveform to an output circuit;

delivering the output waveform from the output circuit; and selectively dissipating some of the previously transferred energy from the output circuit of before that energy is converted into the output waveform.

62. A method as defined in claim 61, further comprising:

selectively dissipating some of the energy previously transferred to the output circuit after delivery of the output waveform has commenced from the energy represented by the drive pulses of one delivered generated mode cycle pattern.

63. A method as defined in claims 37, 39, 41, 43 or 51, further comprising:

obtaining the sample values at a sampling rate which is less than a Nyquist rate for a primary radio frequency of the output waveform.

64. A method as defined in claim 63, further comprising:

obtaining sample values corresponding to both the analog output voltage and the analog output current;

performing a calculation which includes a root mean square calculation using the sample values corresponding to both the analog output voltage and the analog output current to derive an average power value related to the actual power output level; and establishing the pulse-defining value in relation to the average power value.

65. A method as defined in claim 64, further comprising:

establishing the pulse-defining value by using a comparison of the average power value and the selected output power level.

66. A method as defined in claims 37, 39, 41, 43 or 51, further comprising:

establishing the pulse-defining value by performing a calculation using the sample values to derive a power-related quantity related to the actual output power level of the delivered output waveform.

67. A method as defined in claim 66, wherein:

calculating an average power value as the power-related quantity by performing a calculation which includes a root mean square calculation using sample values corresponding to both the analog output voltage and the analog output current.

68. A method as defined in claims 37, 39, 41, 43, 51 or 48, further comprising:

obtaining the sample values of the output voltage and the output current on an alternating basis.

69. A method as defined in claims 37, 39, 41, 43, 51 or 50, further comprising:

converting the sample values of the analog output voltage and the analog output current into corresponding digital sample values;

filling a first plurality of memory locations with the plurality of digital sample values obtained from one sampling interval;

filling a second plurality of memory locations with the plurality of digital sample values obtained from the next subsequent sampling interval;

performing a mathematical calculation using the sample values from one of the first and second pluralities of memory locations to derive an average power value representative of the actual output power level of the delivered output waveform during the corresponding one sample interval, and then alternately performing the same mathematical calculation using the sample values from the other one of the first and second pluralities of memory locations to derive an average power value representative of the actual output power of the delivered output waveform during the other one of the sample intervals.

70. A method as defined in claim 69, further comprising:

obtaining a plurality of sample values of output voltage and a plurality of samples of output current during each sample interval;

obtaining one sample value at a time;

obtaining the sample values of the output voltage and the output current on an alternating basis; and sequentially filling the memory locations of each of the first and second pluralities of memory locations with the sample values in the order in which the sample values are obtained.

71. A method as defined in claims 37, 39, 41, 43, 51 or 50, further comprising:

obtaining a plurality of sample values of the output voltage and a plurality of sample values of the output current during each sampling interval;

calculating an error value during each sampling interval by subtracting from the selected output power level a power value obtained from a calculation using the plurality of sample values obtained during one sampling interval;

retaining a preceding pulse-defining value and a preceding error value applicable to a preceding sampling interval which preceded a present sampling interval in which the sampling routine is presently obtaining the sample values;

designating the error value obtained from the calculation of the error value during a present sampling interval as a present error value; and establishing a present pulse-defining value during the present sampling interval by performing a calculation which includes multiplying the present error value and the preceding pulse-defining value and a first compensating factor and thereafter subtracting the product of the preceding error value and the preceding pulse-defining value and a second compensation factor.

72. A method as defined in claims 37, 39, 41, 43, 51 or 50, further comprising:

establishing the pulse-defining value during each sampling interval by performing a calculation using the plurality of sample values obtained;

establishing a voltage level for converting the energy represented by the drive pulses into the output waveform;

establishing the voltage level in a coordinated relationship with a preferred pulse-defining value;

establishing the preferred pulse-defining value in relation to a present pulse-defining value established during a present sampling interval;

calculating a present voltage error value during the present sampling interval by comparing the present pulse-defining value with the preferred pulse-defining value during the present sampling interval; and adjusting the voltage level relative to an existing voltage level by adding to the existing voltage level an amount obtained by performing a calculation which includes multiplying the present voltage error value and a first compensating factor and by thereafter subtracting the product of a second compensating factor and a preceding voltage error value obtained by the same calculation performed during a preceding sampling interval.

73. A method as defined in claims 37, 39, 41, 43, 51 or 50, further comprising:

performing at least some of the recited steps by executing instructional code using a controller, the instructional code including a plurality of routines which cooperatively create the drive pulses in response to the selected output power level and the selected mode of operation and the actual output power level of the delivered output waveform, the routines and operations executed by the controller comprise:

a sampling routine which obtains a plurality of time-spaced sample values corresponding to the analog output voltage and the analog output current of the output waveform at the time when each sample value is obtained;

a pulse control routine which establishes a pulse-defining value for the drive pulses by performing a calculation using the sample values to derive a power-related quantity related to the actual output power level of the delivered output waveform and a comparison to the selected output power level, a pattern generation routine which generates a mode cycle pattern for a plurality of the drive pulses in accordance with the selected mode of operation; and a pattern delivery routine which creates the drive pulses by sequentially delivering the multiple ones of the generated mode cycle pattern with the drive pulses of the delivered mode cycle patterns having the established pulse-defining value.

* * * * *